United States Patent [19]

Takahashi et al.

[11] Patent Number: 5,046,495
[45] Date of Patent: Sep. 10, 1991

[54] HIGH FREQUENCY HEAT THERAPY SYSTEM

[75] Inventors: Noriyuki Takahashi, Kyoto; Jun Shimoyama, Uji; Eiji Kasai, Muko; Akitoshi Miki, Ibaraki, all of Japan

[73] Assignee: Omron Tateisi Electronics Co., Kyoto, Japan

[21] Appl. No.: 332,925

[22] Filed: Apr. 4, 1989

[30] Foreign Application Priority Data

| Apr. 4, 1988 | [JP] | Japan | 63-82485 |
|---|---|---|---|
| Jul. 9, 1988 | [JP] | Japan | 63-171599 |
| Jul. 9, 1988 | [JP] | Japan | 63-171600 |
| Aug. 24, 1988 | [JP] | Japan | 63-209892 |
| Aug. 26, 1988 | [JP] | Japan | 63-112467 |

[51] Int. Cl.$^5$ .................. A61N 1/00; A61G 13/08
[52] U.S. Cl. .................. 128/399; 128/400; 128/804; 269/322
[58] Field of Search ........... 128/362, 376, 399, 400, 128/401, 804; 600/9, 10; 269/322, 323, 324, 327, 328

[56] References Cited

U.S. PATENT DOCUMENTS

| 4,140,130 | 2/1979 | Storm, III | 128/400 |
|---|---|---|---|
| 4,230,129 | 10/1980 | LeVeen | 128/804 |
| 4,397,314 | 8/1983 | Vaguine | 128/399 |
| 4,434,341 | 2/1984 | Busby | 128/804 |
| 4,638,436 | 1/1987 | Badger et al. | 128/401 |
| 4,672,980 | 6/1987 | Turner | 128/804 |
| 4,823,774 | 4/1989 | Grasser | 269/322 |
| 4,891,483 | 1/1990 | Kikuchi et al. | 128/399 |

FOREIGN PATENT DOCUMENTS

| 0021415 | 1/1981 | European Pat. Off. . |
|---|---|---|
| 0034735 | 9/1981 | European Pat. Off. . |
| 0125495 | 11/1984 | European Pat. Off. . |
| 0214015 | 8/1987 | European Pat. Off. . |
| 0241619 | 10/1987 | European Pat. Off. . |
| 0255645 | 2/1988 | European Pat. Off. . |
| 1466874 | 6/1969 | Fed. Rep. of Germany . |
| 3306391 | 8/1984 | Fed. Rep. of Germany . |
| 3532678 | 3/1987 | Fed. Rep. of Germany . |
| 3721187 | 1/1988 | Fed. Rep. of Germany . |
| 90/00419 | 1/1990 | World Int. Prop. O. . |

*Primary Examiner*—Edward M. Coven
*Assistant Examiner*—Jessica J. Harrison
*Attorney, Agent, or Firm*—Fish & Richardson

[57] ABSTRACT

A high frequency heat therapy system, comprising: an applicator equipped with an electrode and a bolus bag; a high frequency generator unit for generating high frequency electric current that is to be applied to the electrode; a therapeutic table for adjustably supporting a patient; an applicator support unit for adjustably applying the applicator to the patient; a therapeutic data input unit for specifying therapeutic data including those related to positioning of the therapeutic table and the applicator support unit; a therapeutic data storage unit for storing therapeutic data including the data on positioning of the therapeutic table and the applicator; a drive control unit for drivingly controlling the therapeutic table and the applicator support unit according to the data on positioning of the therapeutic table and the applicator stored in the storage unit; and a central control unit for transmitting data stored in the therapeutic data storage unit and, if any, the therapeutic data specified by the therapeutic data input mean to the drive control unit. A high level of reproducibility can be achieved and the contributions of various therapeutic data can be evaluated in a rational way.

13 Claims, 22 Drawing Sheets

HIGH FREQUENCY HEAT THERAPY SYSTEM

TECHNICAL FIELD

The present invention relates to a high frequency heat therapy system for heating and destroying cancer tissues and other malignant body tissues by applying high frequency electric current thereto, and in particular to such a system which permits heat therapies to be conducted with improved reproducibility.

BACKGROUND OF THE INVENTION

According to heat therapeutic systems based on inductive heating, the ailing part is interposed between a pair of planar electrodes, and the cancerous or tumorous tissues of the ailing part is necrotized through heating by applying high frequency electric current between the two electrodes. In reality, however, the electrodes are not directly applied to the patient but by way of bolus bags in which cooling water is circulated. This is for the purpose of cooling the subcutaneous fatty tissues immediately under the electrodes which tend to be heated (because the subcutaneous fatty tissues have a relatively high resistivity with respect to high frequency electric current) as well as the electrodes which also tend to be heated up. A unitized assembly consisting of a bolus bag and an electrode is called as an applicator.

As a conventional heat therapeutic system, there is known the system comprising a bed (therapeutic table) for supporting a patient, an applicator support unit (of the so-called gantry type of the C-arm type which is described hereinafter) for supporting the applicators, a high frequency generator unit for generating high frequency electric current for application across the electrodes of the applicators, a cooling system for circulating cooling water in the bolus bags of these applicators, a temperature measuring unit for measuring the temperatures of the bodily part of the patient which is to be treated or the ailing part and its periphery, and a central control unit for controlling the high frequency generator unit and the cooling system. Further, the control unit is provided with a keyboard for entering therapeutic data such as power output of high frequency electric current and so on, a display unit for monitoring the temperature changes of the ailing part and so one, and a printer for printing out such data.

The bed is provided with a mechanism for adjustably setting up various data on supporting the patient, such as the height thereof and the position of the opening through which one of the applicators is to be applied to the patient from below, according to the bodily part of the patient which is to be treated. The opening of the bed is so positioned that one of the applicators may be applied to the ailing part of the patient which faces the bed, for instance the back of the patient when he lies flat on his back on the bed. Meanwhile, the applicator support unit is provided with a mechanism for appropriately determining the points of application, the direction of application, and the application pressure of the applicators as they are applied to the patient.

However, according to conventional systems for high frequency heat therapy, the data for supporting the patient on the bed and the data of applying the applicators on the patient with the applicator support unit is determined manually by the operator of the unit, and even when the data is to be identical, different operators may select therapeutic data which is different from each other in a subtle way. Further, even when the same operator conducts the therapy, the therapeutic data still tends to differ in each run. Therefore, the heat therapy offers poor reproducibility, and the effectiveness of each heat therapeutic session cannot be precisely evaluated because the therapeutic data may not be identical.

Additionally, since the operator has to perform the heat therapy taking into account the therapeutic data recorded in the medical history of each patient, in certain circumstances, the operator may be too absorbed in such considerations to pay a sufficient attention to the well-being of the patient, and a certain safety problems may arise.

As for the beds for supporting the patients during high frequency heat therapy, according to the conventional arrangements, during the intended heat therapy, the patient is placed flat on the mat portion so that his ailing part may be placed in a therapeutic region which is defined in the plane of the mat portion of the bed, and a pair of applicators are applied to the ailing part from above and below. The therapeutic region is required to be a depressed area (or region) which is large enough to pass through the free end of the electrode portion of the lower applicator. Therefore, the ailing part (such as a hip) tends to droop in the therapeutic region when the patient is placed flat on the mat portion. Therefore, before the applicators are applied to the ailing part and the ailing part is therefore supported by the lower applicator, the patient has to exert some efforts to maintain his horizontal posture. However, such an effort is not only very painful to a seriously ill patient but also tends to induce mistakes by the operator due to the haste and efforts required for the placement of the applicators.

According to conventional high frequency heat therapy systems, the operator applies the applicators by visually checking the distances between the applicators and the bodily part of the patient that is going to be treated, and stops the drive motors when he considered that a desired contact pressure has been achieved between the applicators and the bodily part. Therefore, if he stopped the motors prematurely, the contact pressure between the applicators and the bodily part would be insufficient and a desired therapeutic result may not be obtained. On the other hand, if he stopped the motors a moment too late, the contact pressure would be excessive, and it not only would cause considerable discomfort to the patient, but may also injure the patient in extreme cases.

Further, even when an appropriate contact pressure is achieved, since the applicators are mechanically fixed as they are typically moved by screw rods or the like, a considerable discomfort is experienced by the patient as the respiratory movement of his chest and abdomen is restricted by the applicators.

It is desired to minimize the distance between the applicators irrespective of the contour of the patient's body. To this end, the applicator mounts may be provided with adjustable mean for linearly and angularly adjusting the positions of the applicators so as to accommodate the complicated contours of human bodies. In addition, it is also necessary to laterally adjust the applicators without altering the directions of their axial lines for optimum application of high frequency electric current to ailing parts. According to conventional arrangements, such lateral adjustment was either unavailable or highly troublesome to perform. If the orientation of the applicators is not properly adjusted, not only poor therapeutic results may be produced but also considerable discomfort will be caused to the patient.

According to convention applicators, since the bolus bag cannot be closely applied to the body surface of the patient if the body surface in the contact area contains any projections such as tumors or other bodily parts. If any gap exists between the bolus bag and the body surface, and edge effect is produce or, in other words, the areas surrounding such projections are more heated than other parts, and desired therapeutic results may not be obtained.

BRIEF SUMMARY OF THE INVENTION

In view of such problems of the prior art, a primary object of the present invention is to provide a system for high frequency heat therapy which permits improvements in the reproducibility and safety of high frequency heat therapy.

A second object of the present invention is to provide a high frequency heat therapy system which is easy to operate so that the operator may be able to pay more attention to various matters related to the patient.

A third object of the present invention is to provide a high frequency heat therapy system comprising a therapeutic table or a bed for supporting a patient on which a patient can comfortably lay himself without his ailing part drooping into the cavity or the therapeutic region defined in a middle part of the bed for applying an applicator to the patient from below.

A fourth object of the present invention is to provide a high frequency heat therapy system having an improved applicator actuator which can optimally control the contact pressure between the applicators and the patient, and would not restrain the patient even after the applicators are placed in position.

A fifth object of the present invention is to provide a high frequency heat therapy system having an improved applicator actuator which can positively prevent the applicator from applying excessive pressure to the patient.

A sixth object of the present invention is to provide a high frequency heat therapy system having an improved applicator mount which permits orienting the applicator to an optimum direction in a simple way.

A seventh object of the present invention is to provide a high frequency heat therapy system having a bolus bag which can be applied closely upon the body surface of the patient substantially without creating any gap therebetween.

These and other objects of the present invention can be accomplished by providing: a high frequency heat therapy system, comprising: an applicator equipped with an electrode and a bolus bag; high frequency generator means for generating high frequency electric current that is to be applied to the electrode; cooling fluid circulating means for circulating cooling fluid through the bolus bag; a therapeutic table for adjustably supporting a patient; applicator support means for adjustably applying the applicator to the patient; temperature measuring means for measuring the temperature of a bodily part of the patient that is to be treated; temperature control means for processing a temperature signal from the temperature measuring means and controlling the high frequency generator means and the cooling fluid circulating means; therapeutic data input means for specifying therapeutic data including such data related to positioning of the therapeutic table and the applicator support means; therapeutic data storage means for storing therapeutic data including the data on positioning of the therapeutic table and the applicator; drive control means for drivingly controlling the therapeutic table and the applicator support means according to the data on positioning of the therapeutic table and the applicator stored in the storage means; and central control means for transmitting data stored in the therapeutic data storage means and, if any, the therapeutic data specified by the therapeutic data input mean to the drive control means.

According to the high frequency heat therapy system of the present invention, the therapeutic table and the applicator support means are drivingly controlled according to the therapeutic data stored in the therapeutic data storage means so as to determine the height of the therapeutic table and the application points of the applicators. Therefore, the variations in the therapeutic data due to the difference in the operators can be eliminated, and the reproducibility of the therapeutic data for heat therapy can be improved. The therapeutic data may include a value of high frequency power output. Additionally, through simplification of the processes of heat therapy and the resulting reduction in the burden on the operator, the operator can pay more attention to the data of the patient and his well-being and can therefore achieve a high level of safety.

Further, if the central control means includes a display unit for displaying various data on each particular patient who is going to be treated, the operator can get an overview of the medical history of the patient and can make appropriate decisions without being detracted from the operation of the system and the attention to the well-being of the patient.

According to a preferred embodiment of the present invention, the therapeutic table comprises a pair of bed parts which are separated by a therapeutic region for placing a bodily part to be treated is to be placed and retractable support bars extending from mutually opposing parts of the bed parts. Further, each of the support bars comprises a bar member which can move into and away from the therapeutic region, and a belt extending over an upper surface of the bar member and having one end attached to a part of the bed part adjacent to a base end portion of the bar member and another end adapted to be wound upon a winding pulley. The use of the belt contributes to the reduction of friction between the support bar and the bodily part, and a particularly smooth retraction of the support bar is possible.

According to an advantageous arrangement with regards to the drive mechanism for achieving the required movement of the support bars, the support bars comprise a plurality of elongated bar members arranged in mutually parallel relationship, and each of the bar members is provided with a rack which meshes with a pinion which is common to at least two of the bar members.

In such a bed for high frequency medical heat therapy, the therapeutic region is defined in the plane of the therapeutic bed or in the mat surface for supporting the human body, and the support bars are arranged under the mat surface. The support bars are adapted to advance from either end of the therapeutic region into the center of the therapeutic region and withdraw from the latter into the former. For instance, a rack is securely attached to a lower part of each of the support bars, and a pinion coupled with a reversible motor meshes with the rack so that the rack along with the support bar can move between the underside of the mat surface and the therapeutic region by rotation of the pinion. The ailing part of the patient is supported by the support bars which have advanced into the therapeutic region. In this state, a pair of applicators are applied to the upper and lower part of the ailing part. When the electrode portion at the free end of the lower applicator has come to a position adjoining the underside of the support bars, the support bars are withdrawn into the mat surface. The ailing part slightly sags when the support bars are completely withdrawn by losing its support, but is supported by the electrode portion of the lower applicator placed immediately under it. As the electrode portion is gradually lifted thereafter, the horizontal posture of the patient is regained. Therefore, as opposed to the case of the prior art, the patient is not required to exert a significant effort to keep the horizontal posture so that the ailing part may not sag into the therapeutic region until the applicator is placed into its final position, and can therefore lie in the bed with a comfortable posture. As a result, the operator can place the applicators at the precise locations of the ailing parts without undue haste.

According to a certain preferred embodiment of the present invention, the applicator support means comprises an arcuate arm extending around the patient to be treated, and is guided for angular movement along its curved axial line. To the end of permitting the application of the applicators to the patient from a desired angle, the applicator support means comprises angular displacement means for permitting angular displacement of the applicator about a pivot point at a base end portion of the applicator, and a linear displacement means for moving the applicator toward and away from the patient to be treated, and/or the applicator support means comprises lateral displacement means for displacing the applicator laterally from its axial center line.

To reduce the restraint on the patient by the application of the applicators, the applicator support means may further comprise an elastic buffer means for accommodating movement of the patient when the applicator is applied to the patient so as to accommodate the body movement of the patient. Further, to reduce the discomfort to the patient when the applicators are applied to him or, in extreme case, the possibility of injuring the patient from the pressure applied by the applicators, the applicator support means may further comprise drive stop means for stopping movement of the applicator toward the patient to be treated when deformation of the buffer means has exceeded a certain limit.

To achieve a favorable contact between the bodily part to be treated and the electrode, the bolus bag is desired to be substantially larger than the electrode as seen in plan view. In particular, it is desired that the bolus bag is provided with attaching bands extending laterally therefrom so that the two bolus bags interposing a bodily part of a patient therebetween may be connected with each other by means of these attaching bands and a desired state of contact can be achieved between the applicators and the bodily part of the patient.

BRIEF DESCRIPTION OF THE DRAWINGS

Now the present invention is described in the following with reference to the appended drawings, in which.

DETAILED DESCRIPTION OF THE PREFERRED EMBODIMENTS

Figure 1:
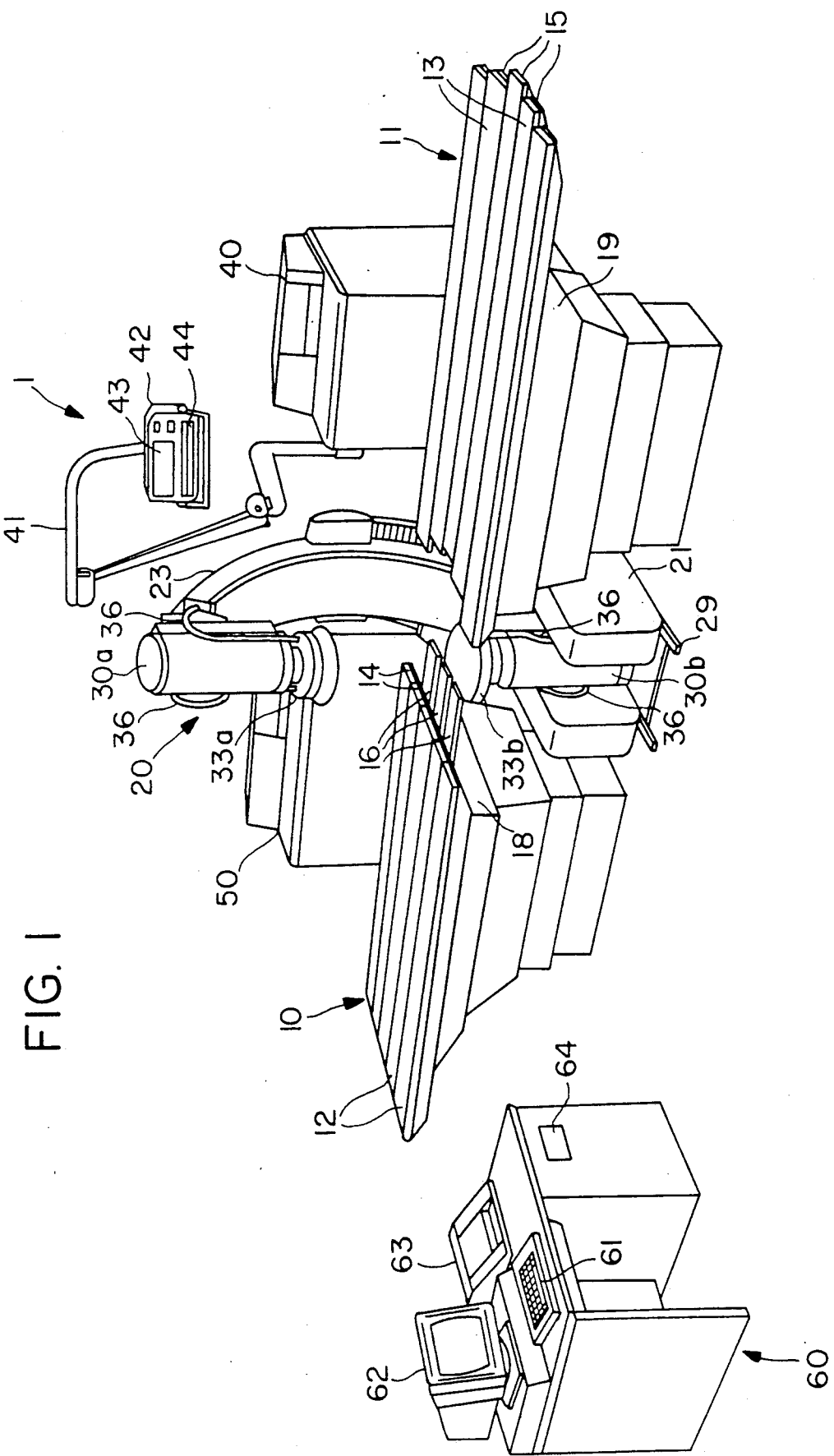
FIG. 1 is general perspective view of an embodiment of the high frequency heat therapy system according to the present invention.

FIG. 1 is an overall perspective view of an embodiment of the high frequency heat therapy system according to the present invention. This heat therapy system 1 comprises two bed parts (therapeutic tables) 10 and 11, an applicator support unit 20, a drive control unit 40, a cooling system 50, a console 60, and a temperature measuring unit 70 and a high frequency generator unit 80 (refer to FIG. 4) which are not shown in FIG. 1. The bed parts 10 and 11 are each provided with a lifting motor (not shown in the drawings) which is controlled by a bed lifting control unit 45a or 45b shown in FIG. 16.

On the upper surfaces of the bed parts 10 and 11 are placed slide mats 12 and 13, respectively, consisting of a plurality of elongated plates arranged in mutually parallel relationship (refer to FIG. 1) on respective mat supports 14 and 15. The mat supports 14 and 15 supporting the slide mats 12 and 13 are in turn supported by bed bases 18 and 19. Each piece of the slide mats 12 and 13 is slidably supported on the mat support 15 or 16 of the corresponding bed part 10 or 11 so as to be manually and individually moved along the longitudinal direction.

Each piece of the slide mats 12 and 13 is provided with a position detection sensor for detecting the position of the corresponding piece of the slide mat 12 or 13, and a stop mechanism for stopping the slide mat piece at a prescribed position (which is not shown in the drawings). The stop mechanism may comprise a rod member which may be fitted into one of a plurality of holes provided in the lower surface of each piece of the slide mats 12 and 13 along its longitudinal direction at equal interval so as to stop the slide mat piece 12 or 13 at the corresponding position. The position detection sensors are connected to slide mat control units 46a and 46b (FIG. 16), and each of the slide mat control units 46a and 46b controls the corresponding stop mechanism.

Figure 5:
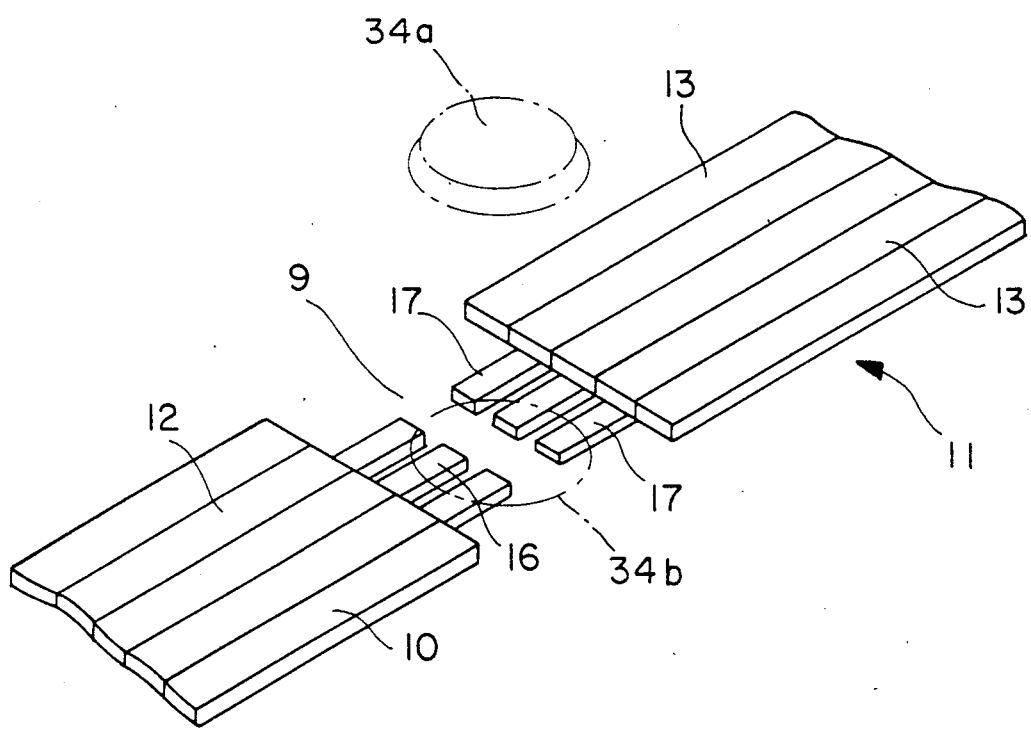
FIG. 5 is a fragmentary perspective view of the support bars.

Each of the bed parts 10 and 11 is provided with support bars 16 and 17 (refer to FIGS. 1 and 5). FIG. 1 shows the state in which only the support bars 16 of one of the bed parts 10 are protruding. The support bars 16 are provided in the mutually opposing faces 10a and 11a of the bed parts 10 and 11. The support bars 16 and 17 are driven by motors so as to be advanced and retracted horizontally along the longitudinal direction of the slide mats 12 and 13 as described hereinafter. These motors are controlled by support bar control units 47a and 47b (refer to FIG. 16).

Figure 3:
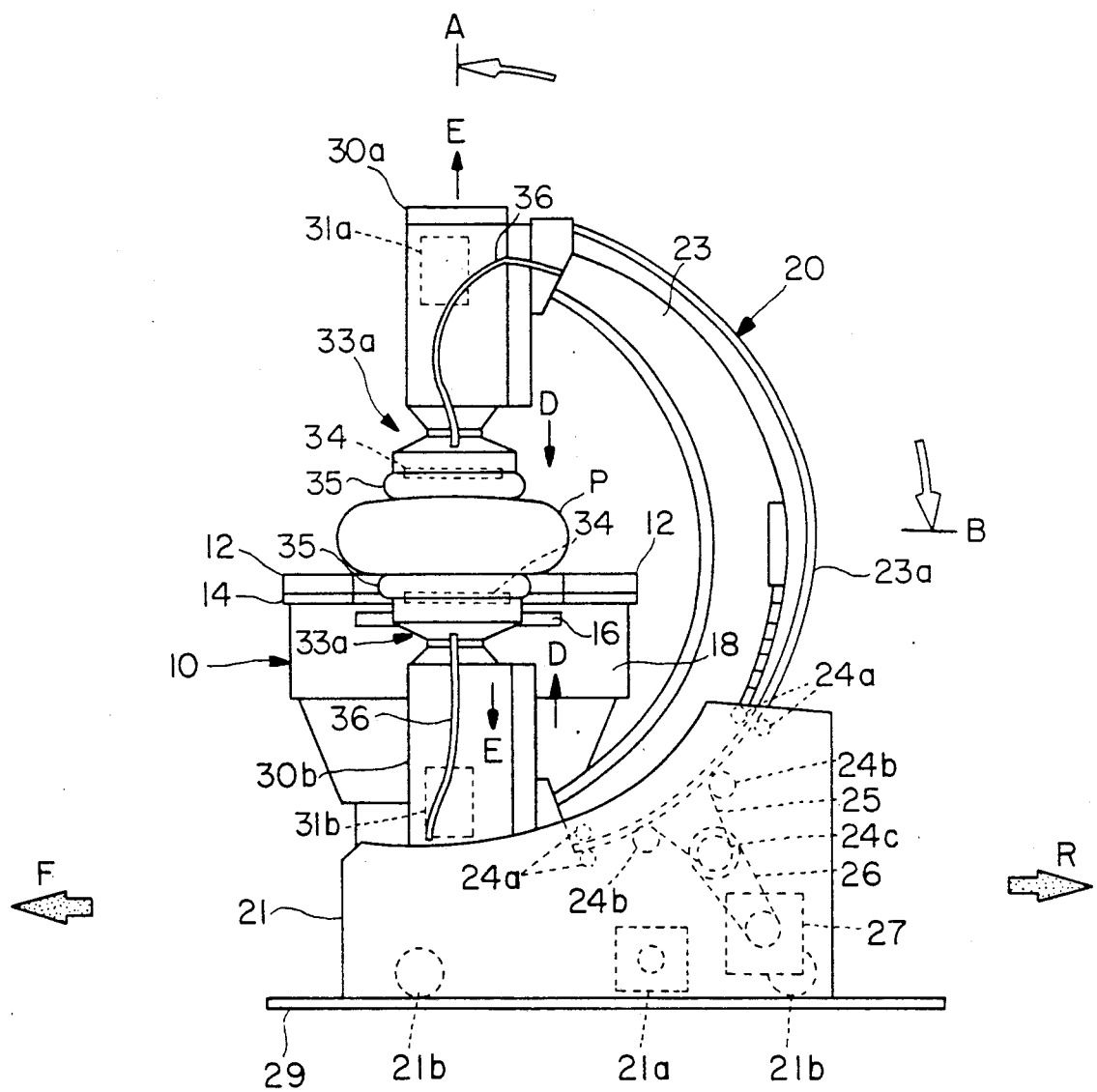
FIG. 3 is an end view of the heat therapy system with one of the bed parts removed.

Numeral 20 denotes a C-arm type applicator support unit as best shown in FIG. 3. This applicator support unit 20 is rotatively carried by a carriage 21 which is slidable along a pair of rails 29. The rail 23a provided in the back of the C-arm 23 is supported by rollers 24a, ..., 24a of the carriage 21 so that the C-arm 23 can rotate between the upright position A illustrated in FIG. 3 and the horizontal position B which is rotated in clockwise direction by approximately 90 degrees therefrom as seen in FIG. 3.

Along the back of the rail 23a of the C-arm 23 extends a chain 25 which is slightly longer than the rail 23a. Each end of the chain 25 is attached to the corresponding end portion of the rail 23a, and the chain itself 25 is passed around the sprockets 24b, 24c and 24b in the carriage 21. The sprocket 24c is drivingly connected to a motor 27 by way of another chain 26 so as to drivingly rotate the C-arm 23 with the motor 27. The motor 27 is controlled by a C-arm rotation control unit 38 shown in FIG. 16.

The carriage 21 is placed on the rails 29 by way of wheels 21b and 21b which may be drivingly rotated by a motor 21a so that the carriage 21 may move laterally as indicated by the arrows F and R in FIG. 3. This movement is controlled by a C-arm linear movement control unit 37.

A pair of applicator mounts 30a and 30b are provided on either end of the C-arm 23. Each of the applicator mounts 30a and 30b is internally provided with a motor 31a or 31b so that the applicator mount 30a or 30b may be moved relative to the corresponding end portion of the C-arm 23 in an applying direction D and a releasing direction E. This movement is controlled by applicator application control units 48a and 48b (refer to FIG. 16).

On each of the applicator mounts 30a and 30b is mounted an applicator 33a or 33b in a detachable manner. Each of the applicators 33a and 33b is provided with an electrode 34 and a bolus bag 35. Numeral 36 denotes a tube for conducting cooling water into and out of the bolus bags 35.

The drive control unit 40 is provided with an arm 41 at the free end of which is mounted an operation board 42 (refer to FIG. 1). This operation board 42 is provided with a display unit 43 and a push button unit 44. The cooling unit 50 is connected to the applicators 33a and 33b via the cooling water tube 36 for circulating cooling water in the applicators 33a and 33b.

The console 60 is provided with an input unit (keyboard) 61, a display unit (CRT display unit) 62, an output unit (printer) 63, and a storage unit (floppy disk drive) 64.

Figure 4:
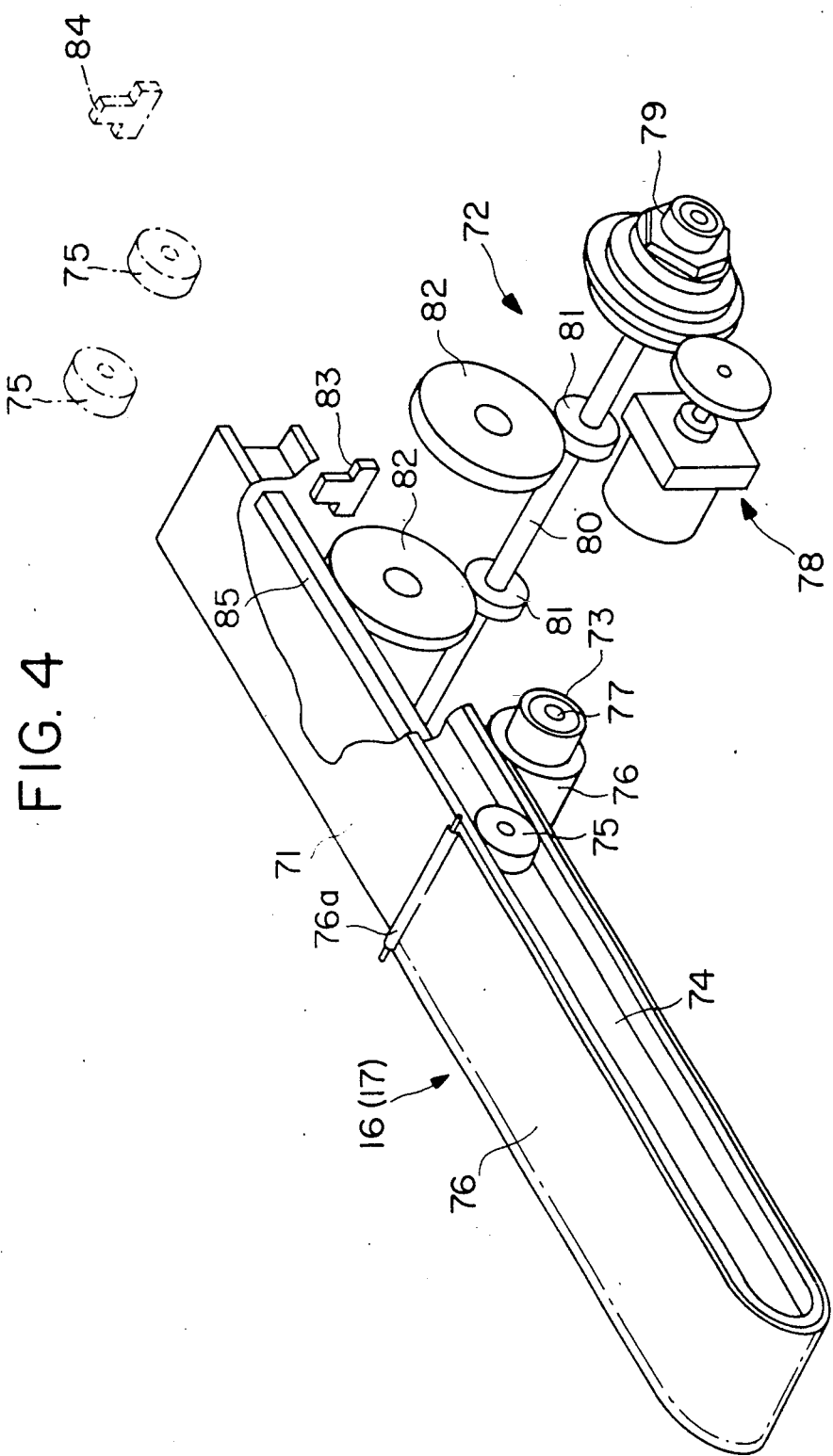
FIG. 4 is partly removed, fragmentary perspective view of one of the support bars and its drive mechanism.
Figure 6:
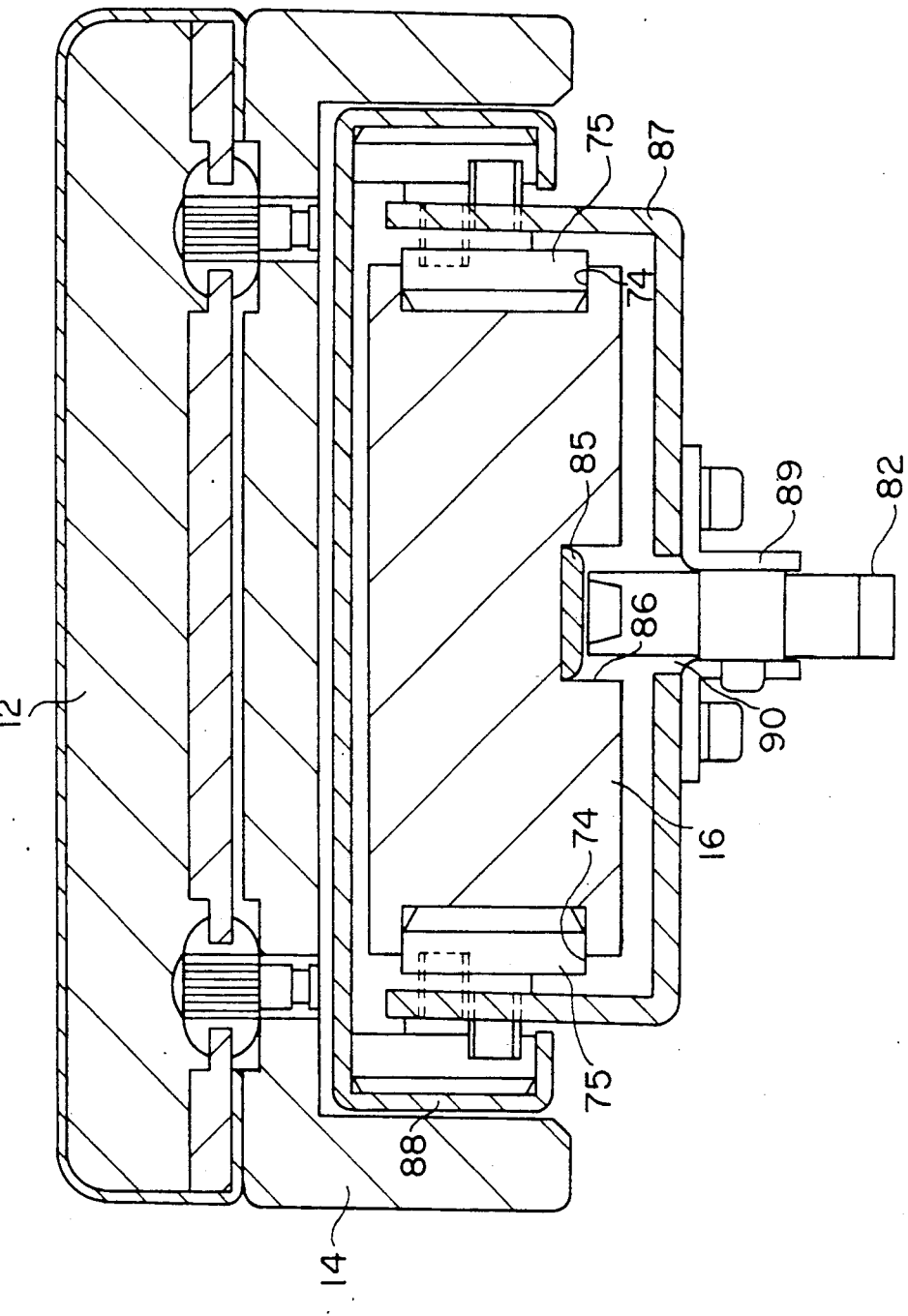
FIG. 6 is a cross sectional view of one of the support bars and its guide mechanism.
Figure 7:
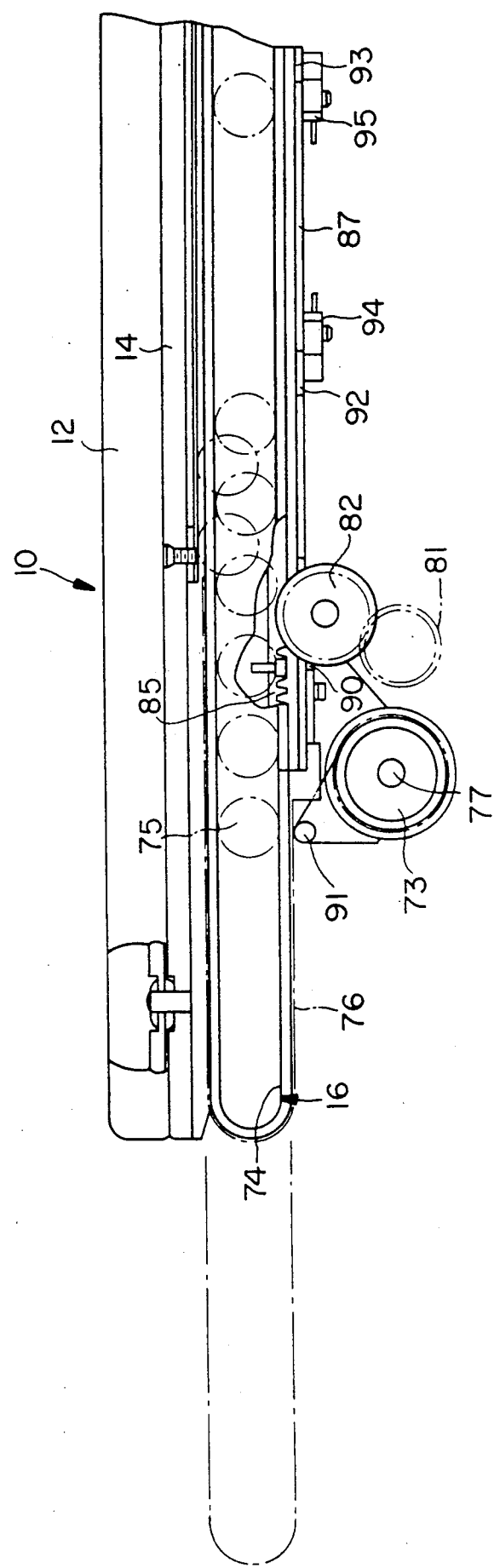
FIG. 7 is partly removed, fragmentary side view of one of the support bars and its drive mechanism.

FIGS. 4 through 6 show the structure of the support bars 16 and 17 in detail.

Each of the support bars 16 and 17 consists of an elongated flat plate having a uniform thickness. and is provided with a pair of grooves 74 on either side thereof for receiving bearing rollers 75 therein. A central part of the lower surface of this support bar 16 is provided with a cavity 86 for receiving a rack 85 which is secured therein. This rack 85 meshes with a pinion 82 which is rotated by a drive mechanism as described hereinafter, and moves the support bar 16 in either longitudinal direction. As shown in the sectional view of FIG. 6, the support bar 16 is surrounded by a pair of frames 87 and 88 each having a rectangular C-shape. In other words, the support bar 16 is received in a region defined by the lower frame 87 and the upper frame 88 when they are fitted one into the other, and the two side walls of the lower frame 87 rotatably support the bearing rollers 75. The lower frame 87 is securely attached to the bed base 18. The pinion 82 is pivotally supported by a flange 89 projecting from the bottom surface of the lower frame 87, and the pinion 82 is protrudes into an opening 90 provided in the bottom wall of the lower frame 87 so as to mesh with the rack 85.

Further, the bottom wall of the lower frame 87 is provided with an out-limit photo micro sensor 94 in a longitudinally central part thereof and an in-limit photo micro sensor 95 at a base end thereof so that the longitudinal movement of the support bar 16 may be controlled by receiving the light projected from the light emitting parts of the sensors 94 and 95 and reflected by the bottom surface of the support bar 16 with their light receiving parts through an opening 92 or 93 provided in the bottom wall of the lower frame 87. In other words, the output signals from the sensors 93 and 94 stop the operation of the drive mechanism (a reversible motor 78) 72 which is described hereinafter.

FIG. 4 is a perspective view for illustrating the relationship between one of the support bars 16 and the drive mechanism 72 for the support bar 16.

The drive mechanism 72 is disposed under the support bar 16 or under the lower frame 87, and comprises a reversible motor 78, a rotary shaft 80 provided with a torque limiter 79 and adapted to be driven by the reversible motor 78, and a transmission gear 81 mounted on this rotary shaft 80 so as to mesh with the pinion 82. The drive force from the reversible motor 78 rotates the rotary shaft 80 along with the drive gear 81, and the pinion 82 in turn moves the rack 85 or the support bar 16 into and away from the therapeutic region 19 defined between the two bed parts 10 and 11.

Under the support bar (the lower frame 87) 16 and in a longitudinally central part thereof is disposed a belt winding drum 73 on which a highly self-lubricating resin belt 76 is wound. The front end of this belt 76 is passed around the front end of the support bar 16 from below after passing by a guide roller 91, and is fixedly secured to an appropriate location of the longitudinally central part of the upper surface of the upper frame 88. The rotary shaft 77 of the winding drum 73 is provided with a spiral spring (not shown in the drawings) for producing a winding torque in such a manner that the belt 76 is paid out from the winding drum 73 against its spring force by the amount corresponding to the advance of the support bar 16 when it is advanced into the therapeutic region 19 and is taken up by the winding drum 73 by the amount corresponding to the withdrawal of the support bar 16 by its spring force. The fact that this self-lubricating belt 76 covers the upper surface of the support bar 16 permits smooth withdrawing of the support bar 16 which is in contact with the patient.

According to the present invention, as described above, since the support bars 16 and 17 for supporting the ailing part are arranged so as to advance into and withdraw from the therapeutic region 19a defined in the plane of the beds, the patient can keep a comfortable posture simply by lying on the bed with his ailing part placed upon the support bars 16 and 17 which have been advanced into the therapeutic region 19 reserved for therapeutic purpose.

Therefore, the present invention can remove the problems of the prior art such that the ailing part tended to sag into the therapeutic region and that the patient had to exert a considerable effort to keep a horizontal posture so as not to sag into the therapeutic region. Furthermore, since the patient can achieve a natural horizontal posture simply by lying on the bed, the operator can accurately place the applicators upon the ailing part without any undue haste, and the possibility of misoperation is eliminated. Thus, the present invention can achieve the object of the present invention, and can offer various advantages.

Figure 8:
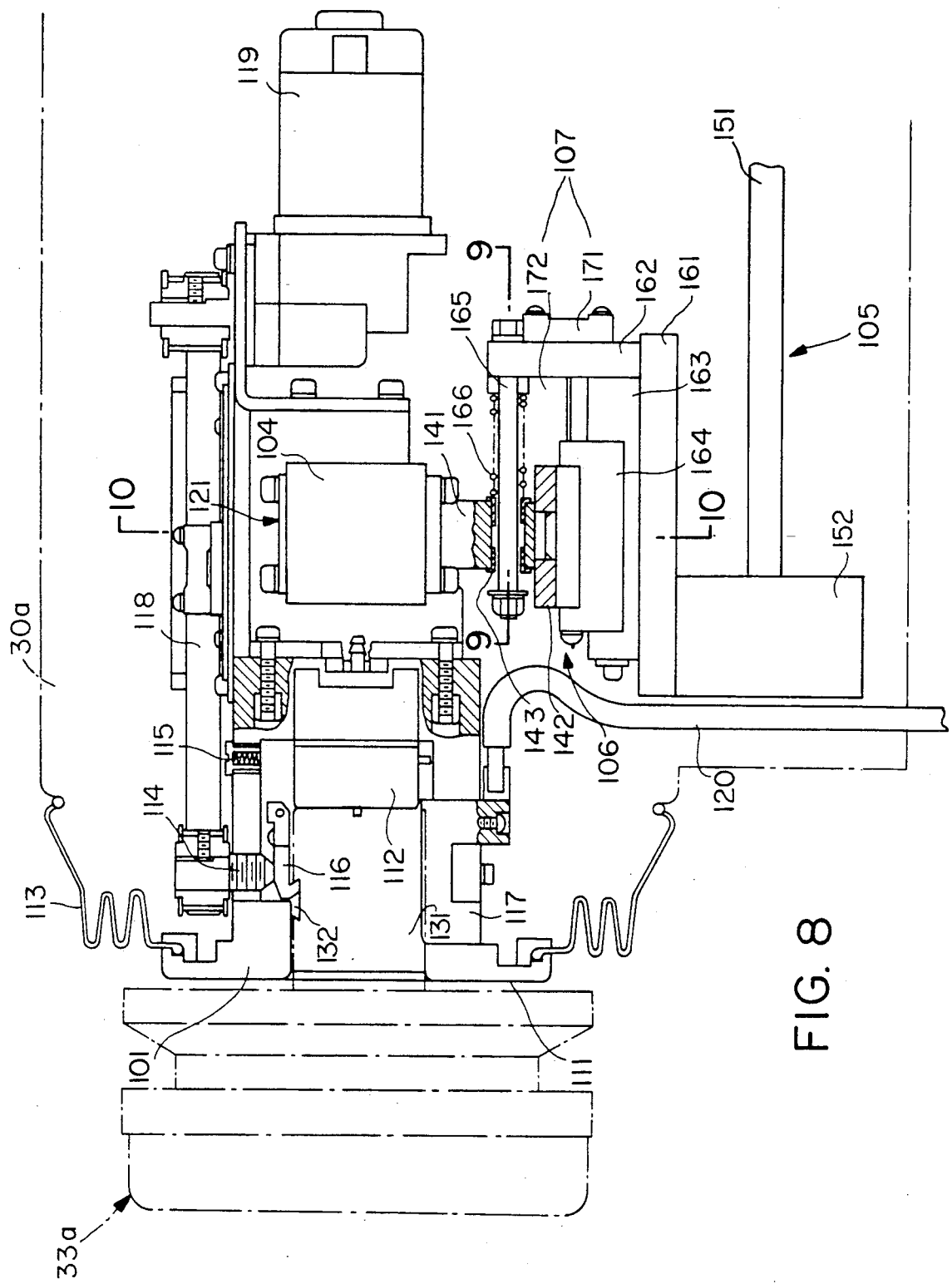
FIG. 8 is a sectional side view of one of the actuators for applying the applicators upon the patient.
Figure 9:
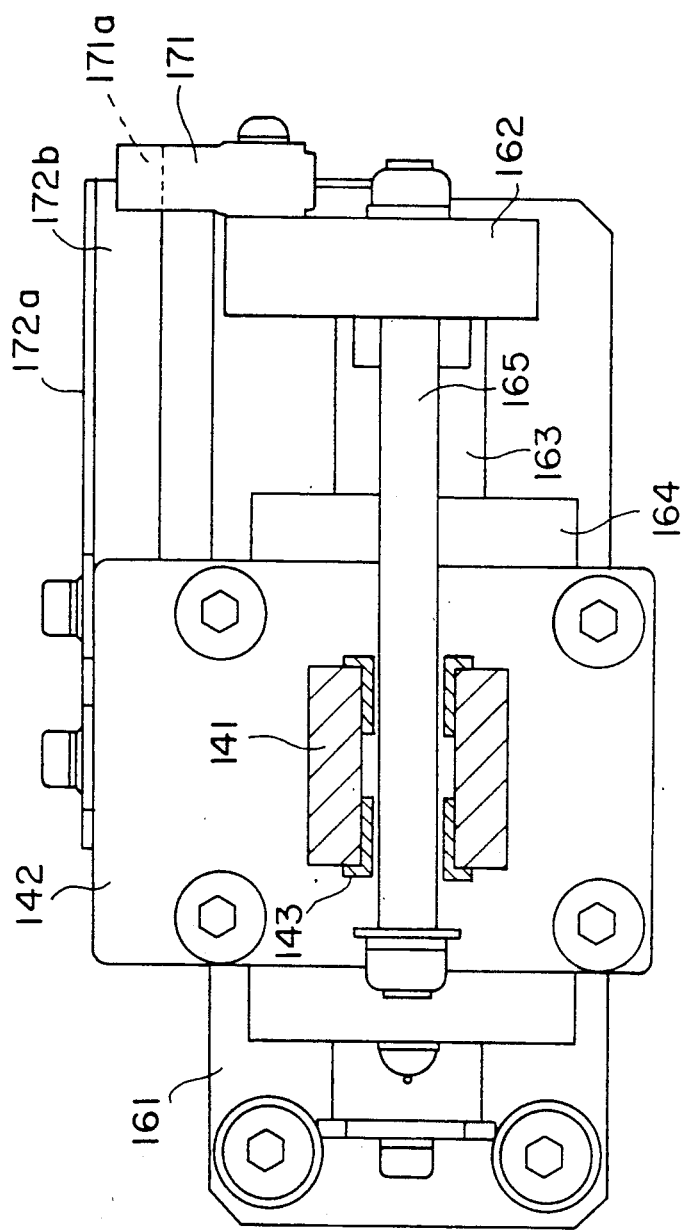
FIG. 9 is a sectional view taken along line 9—9 of FIG. 8.
Figure 10:
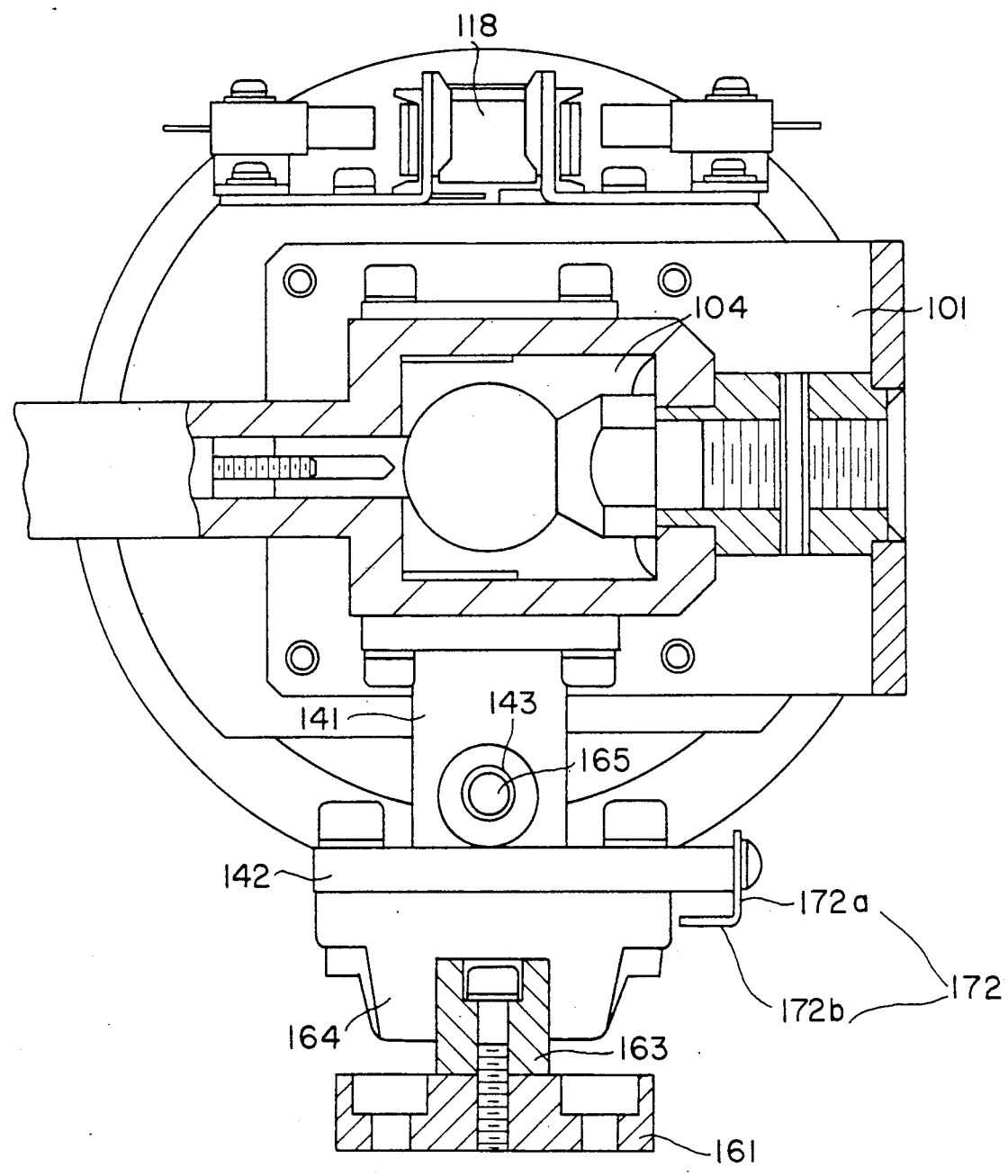
FIG. 10 is a sectional view taken along line 10—10 of FIG. 8.
Figure 11:
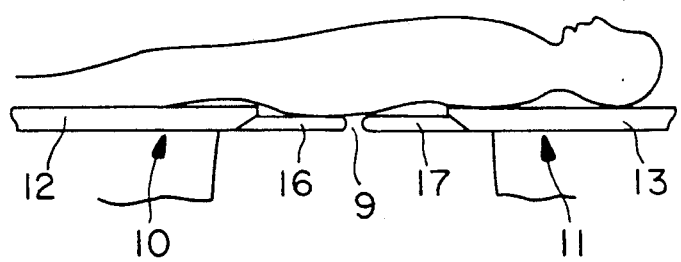
FIGS. 11 through 14 are schematic front views of the heat therapy system showing how the patient is supported by the two bed parts in time sequence.

FIGS. 8 through 10 show the actuator for applying the applicators 33a and 33b to the patient. This actuator comprises an electrode hidden in the applicator 33a, an electrode mount 101, a linear drive unit 105, a slide unit 106, and stop control unit 107, and an angular drive unit 104.

As shown in FIG. 8, the electrode mount 101 is annular in shape, and is received in a cylindrical casing of the applicator mount 30a, and an axial end of the electrode mount 101 defining an electrode mounting hole 112 is exposed out of a flexible sleeve 113 which is fitted between the peripheries of the electrode mount 101 and the casing of the applicator mount 30a. The electrode has a disk-shaped main body and a coaxial mounting rod 131 extending from its rear surface. An annular groove 132 is provided in the outer circumferential surface of this mounting rod 131, and the mounting rod 131 itself is received in the mounting hole 112 of the electrode mount 101. The flexible sleeve 113 permits angular and linear movement of the electrode mount 101 while keeping the interior of the casing of the applicator mount 30a sealingly enclosed from the exterior.

The electrode mount 101 is provided with a threaded stopper rod 114 which can project laterally into the mounting hole 112, and a high frequency power supply unit 117 adjacent to the outer end of the mounting hole 112. The threaded stopper rod 114 is connected to a reversible motor 119 via suitable transmission means such as a belt and pulley mechanism 118 so as to move toward and away from the mounting rod 131. Adjacent to the front end of the stopper rod 114 is pivotally supported a pawl 116 which is adapted to engage the annular groove 132 provided in the mounting rod 131 and to thereby secure the mounting rod 131 in the mounting hole 112 when the front end of the stopper rod 114 is pressed upon the back of the pawl 116. The high frequency power supply unit 117 is connected to a high frequency power source not shown in the drawings via lead wires 120 and electric connection between the high frequency power supply unit 117 and the mounting rod 131 or the electrode is ensured by their mutual contact through the pressure applied from the stopper rod 114 via the pawl 132.

Further, a lateral hole 121 is provided laterally through the mounting hole 112, and the angular drive unit 104 is received in this lateral hole 121. The angular drive unit 104 permits the electrode mount 101 to be angularly moved both in any lateral direction relative to the axial line of the applicator mount 30a by way of a ball and socket coupling and a motor. The support shaft 141 for this angular drive unit 104 extends laterally and it is securely attached to a support plate 142 at its free end. This support plate 142 is securely attached to the slide unit 106 which is described hereinafter.

The linear drive unit 105 comprises a linear drive rod 151 which is connected to a motor (not shown in the drawings) via rotary-linear movement conversion means, and the axial movement of the linear drive rod 151 causes the linear movement of the slide unit 106 and the electrode mount 101.

A primary feature of this embodiment is found in the slide unit 106 and its control unit 107 which intervene between the slide unit 6 and the electrode mount 101.

The slide unit 106 is provided with a wall member 162 which extends laterally from an end of a mounting plate 161 which is in turn mounted on a mounting flange 152 of the drive rod 151. A rail 163 having a rectangular cross section is securely attached to the mounting plate 161, and a slider 164 rides over it in a freely slidable manner as best shown in FIGS. 8 and 10. Further, a stopper shaft 165 projects axially longitudinally from the wall member 162 and is received by a bore provided in the support shaft 141 via bushes 143. A compression coil spring 166 is wound around the stopper shaft 165 so as to be interposed between the support shaft 141 and the wall member 162. The support plate 142 is fixedly secured to the slider 164 by means of threaded bolts as shown in FIG. 9. Thus, the entire electrode mount 101 is urged towards the electrode, and the slide unit 106 and the electrode mount 101 are adapted to be driven linearly and simultaneously by the linear drive unit 105 as a single body in the direction to push the electrode out of the mounting hole 112.

The control unit 107 comprises a photo micro sensor 171 mounted on an end portion of the wall member 162, and a light shield 172 which mounted on the support plate 142. The photo micro sensor 171 is provided with a slot 171a as shown in FIG. 9 and a light emitting element and a light receiving element (not shown in the drawings) are mounted on mutually opposing wall surfaces of the slot 171a. Meanwhile, the light shield 172 is shaped as letter L and comprises a mounting piece 172a and an active piece 172b; the mounting piece 172a is fixedly attached to the wall member 162 and the active piece 172b moves into and out of the slot 171a. Therefore, the light shield 172 normally does not block the light of the photo micro sensor 171 and the electrode is in contact with the bodily part to be treated. When the electrode mount 101 is pushed into the casing of the applicator mount 30a by the reaction from the contact between the electrode 103 and the bodily part to be treated as the applicator 33a is pressed upon the bodily part to be treated, the electrode mount 101 is retracted against the spring force of the slide unit 106 and the light shield 172 blocks the light of the photo micro sensor 171.

Therefore, according to this structure, when the linear drive rod 151 is extended by the applicator application control unit 48a or 48b, the slide unit 106, the electrode mount 101 and the electrode move toward the patient as an integral body. When the electrode has come into contact with the patient, the reaction acting upon the electrode drives the electrode and the electrode mount 101 backward against the spring force of the compression coil spring 166. The slider 164 attached to the electrode mount 101 also moves back on the rail 163. Further, since the linear drive unit 105 which caused the extension of the linear drive rod 151 is still operating, the compression coil spring 166 becomes considerably compressed. In other words, the the electrode mount 101 or the support rod 141 comes close to the wall member 162. As a result, the light shield 172 is moved into the slot 171a and blocks the light of the photo micro sensor 171. The photo micro sensor 171 in turns supplies a stop signal to the linear drive unit 105, and the extension of the linear drive rod 151 is immediately discontinued. Thus, the electrode can contact the patient's bodily part which is to be treated with an appropriate pressure so that the risk of injuring the patient is eliminated on the one hand and poor therapeutic results due to insufficient contact pressure can be avoided on the other hand.

Furthermore, when the patient's body is moved, for instance due to the respiratory activity of the patient, the electrode mount 101 along with the electrode can move according to the movement of the bodily part of the patient in question and the electrode can thus accommodate the movement of the bodily part without applying undue pressure or discomfort to the patient.

Now the operation of the bed parts 10 and 11 and the support bars 16 and 17 is described in the following with reference to FIGS. 4 through 8 and FIGS. 11 through 14.

Figure 12:
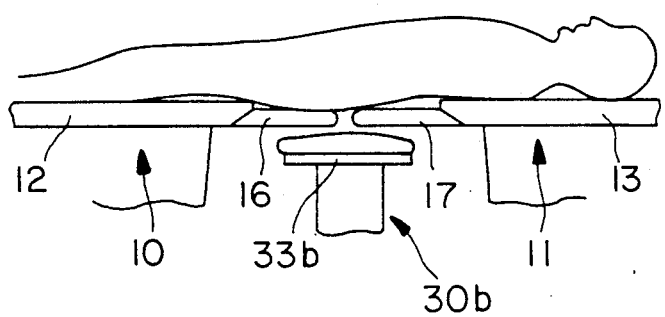

In performing a medical heat therapy on an ailing bodily part by using a bed for high frequency medical heat therapy having such a structure, first of all, the support bars 16 and 17 are advanced from the respective undersides of the mats 12 and 13 into the region defined between the opposing faces of the bed parts 10 and 11 or the therapeutic region 19. This is accomplished by driving the reversible motor 78 and rotating the pinion 82 so as to advance the racks 85 or the support bars 16 (and 17). At this moment, the belts 76 are taken out by the advancement of the support bars 16, and the upper surfaces of the support bars 16 are covered by the belts 76. When the base end of each of the support bars 16 has passed the corresponding out-limit photo micro sensor 94 (the opening 93), the reflected light is blocked by the support bars 16, and the motor 78 is stopped by the stop signal supplied from the sensor 94. At this moment, the front end of each of the support bars 16 has advanced to the desired point in the therapeutic region 19. Then, the patient is laid across the beds 10 and 11 so that his bodily part that is to be treated may be placed on the support bars 16 and 17 as shown FIG. 11. Thereafter, the pair of applicators 33a and 33b are placed upon the ailing part, and interposes the ailing part between the two applications 33a and 33b. Specifically, the lower applicator 33b is placed immediately below the support bars 16 and 17 as shown in FIG. 12. In the meantime, the ailing part of the patient located in the therapeutic region 19 is completely supported by the support bars 16 and 17. Therefore, the patient is positively prevented from sagging into the therapeutic region 19.

Then, the racks 85 or the support bars 16 and 17 are withdrawn by reversing the reversible motor 78. During this process, since the ailing part of the patient is in contact with the highly self-lubricating belts 76, very little friction is caused by this withdrawing movement, and the support bars 16 and 17 can therefore smoothly withdraw. The corresponding span length of the belts 76 is accordingly wound upon the winding drums 73 by means of the restoring force of the spiral springs. When the support bars 16 and 17 are completely withdrawn or when the therapeutic region 19 has been completely opened up as it originally was, the in-limit photo micro sensor 28 detects the light reflected by the base end of the support bar 16. As a result, a stop signal is supplied to the motor 78 to stop it.

Figure 13:
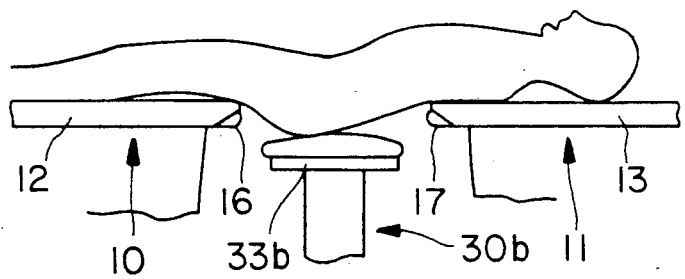
Figure 14:
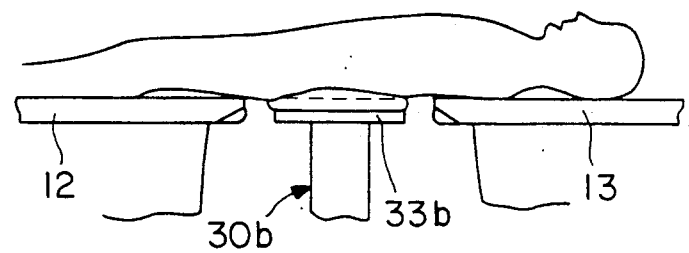

When the therapeutic region 19 is completely opened up, the ailing part of the patient slightly sags down due to the loss of the supporting member as shown in FIG. 13. However, at this moment, the lower applicator 33a is already placed immediately below the ailing part. Therefore, the ailing part which may have slightly sagged down is immediately supported by the lower applicator 33b as shown in FIG. 13, and the patient is kept in a horizontal posture thereafter by lifting the lower electrode applicator 33b as shown in FIG. 14.

Figure 15:
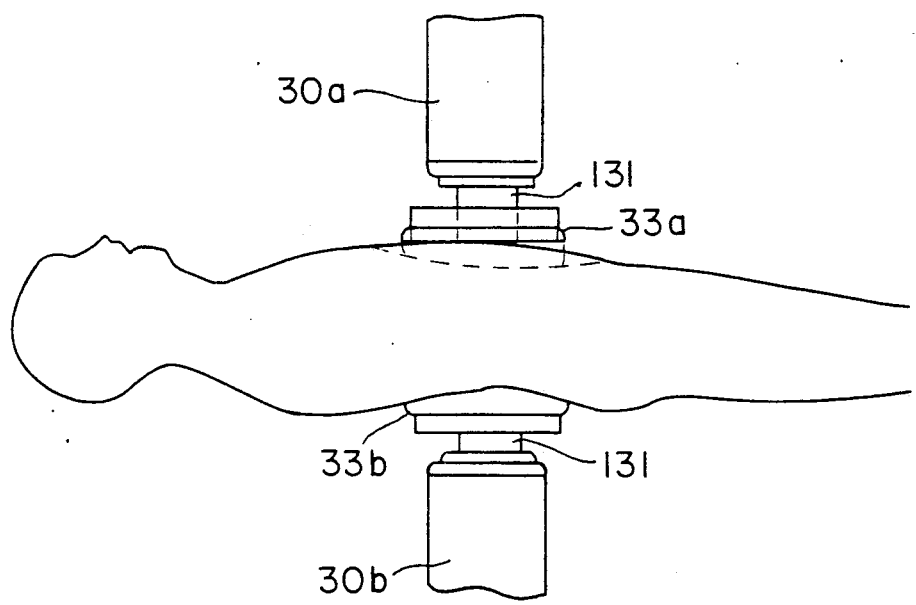
FIG. 15 is a schematic side showing how the applicators may be applied upon the patient.

FIG. 15 shows the two applicators 33a and 33b placed in position for heat therapy. As shown in this drawing, the bodily part is slightly depressed due to the pressure from the applicators 33a and 33b which is determined by the elastic force of the compression coil spring 166, and the patient does not experience any undue discomfort by the pressure from the applicators as the movement of the patients body can be accommodated by the compression coil spring 166.

Figure 16:
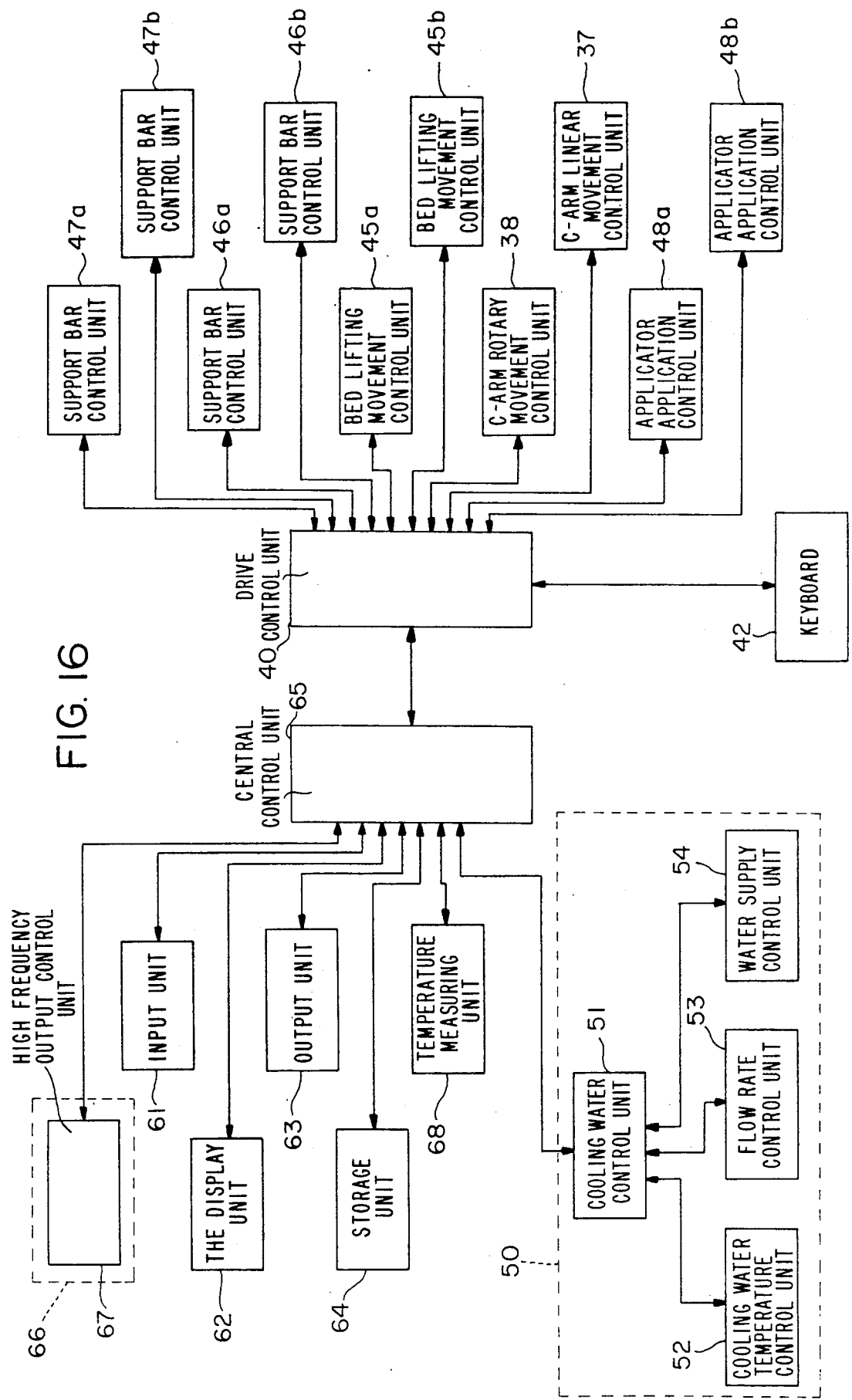
FIG. 16 is a block diagram showing the control structure of the high frequency heat therapy system according to the present invention.

FIG. 16 is a block diagram showing the overall circuit structure of the heat therapy system of the present embodiment. To a central control unit 65 are connected the input unit 61, the display unit 62, the output unit 63 the storage unit 64, the temperature measuring unit 68, a cooling water control unit 51 for the cooling unit 50, and an electromagnetic output control unit 67 for the high frequency generator unit 66. The central control unit 65 has the functions of processing therapeutic data, reading and storing thereapeutic data from and into the storage unit 64, controlling the input from the input unit 61, and transferring therapeutic data (such as cooling water temperature, flow rate, amount of water supply, high frequency output and so on) to the cooling system 50 and the high frequency generator unit 66.

To the cooling water control unit 51 of the cooling unit 50 are further connected a water temperature control unit 52, a flow rate control unit 53, and a water supply control unit 54 for controlling the water temperature and flow rate of the cooling water circulating in the applicators 33a and 33b, and the amount of the cooling water which is supplied to each of the bolus bags 35.

To the central control unit 65 is connected the drive control unit 40 so that those therapeutic data related to the bed parts 10 and 11 and the applicator support unit 20 is transmitted from the central control unit 65 to the drive control unit 40. To the drive control unit 40 are connected the aforementioned slide mat control units 47a and 47b, the support bar control units 46a and 46b, the bed lifting movement control units 45a and 45b, the C-arm linear movement control unit 37, the C-arm rotary movement control unit 38, and the applicator application control units 48a and 48b.

Figure 17:
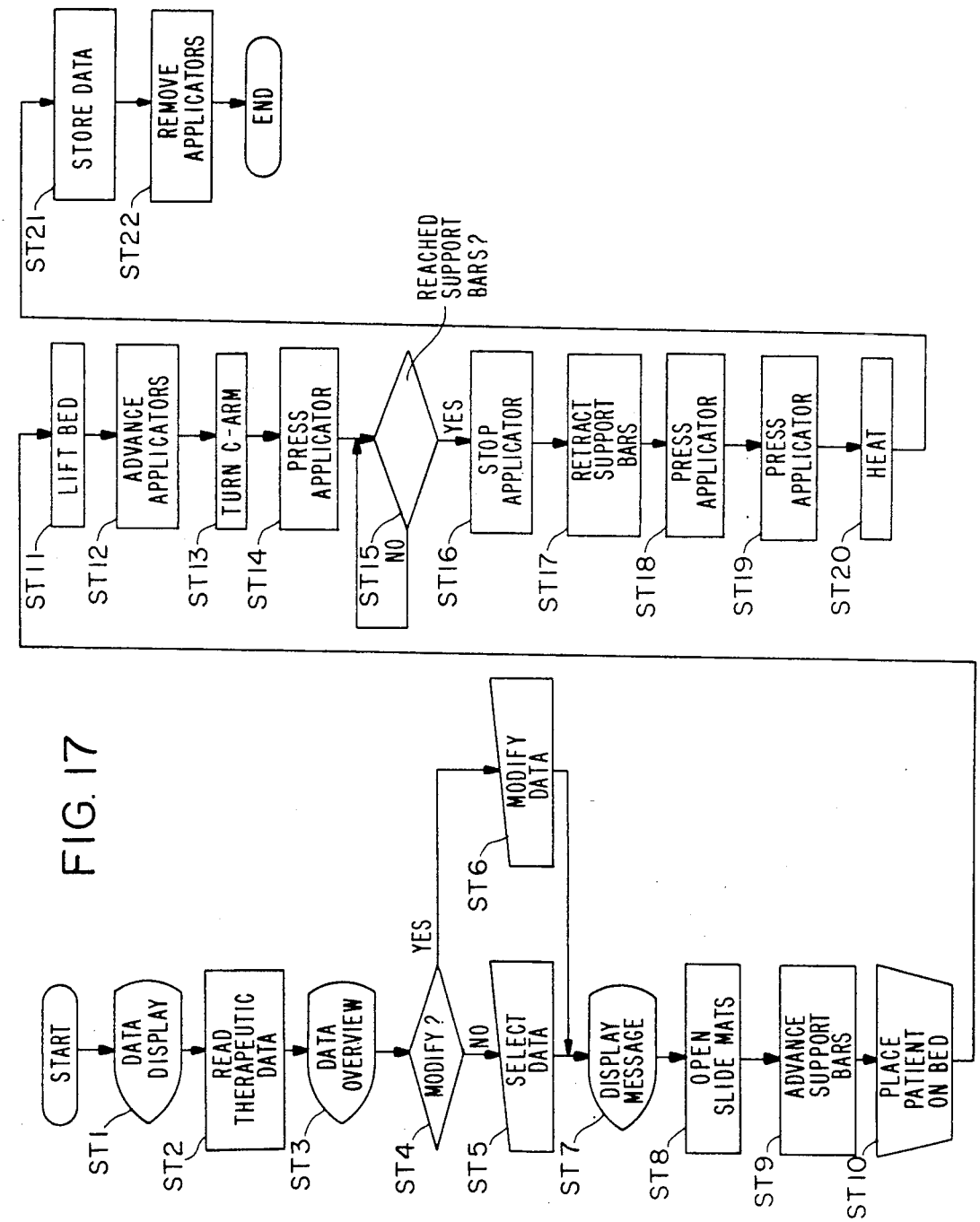
FIG. 17 is a time chart showing the operation of the control structure shown in FIG. 16.
Figure 18:
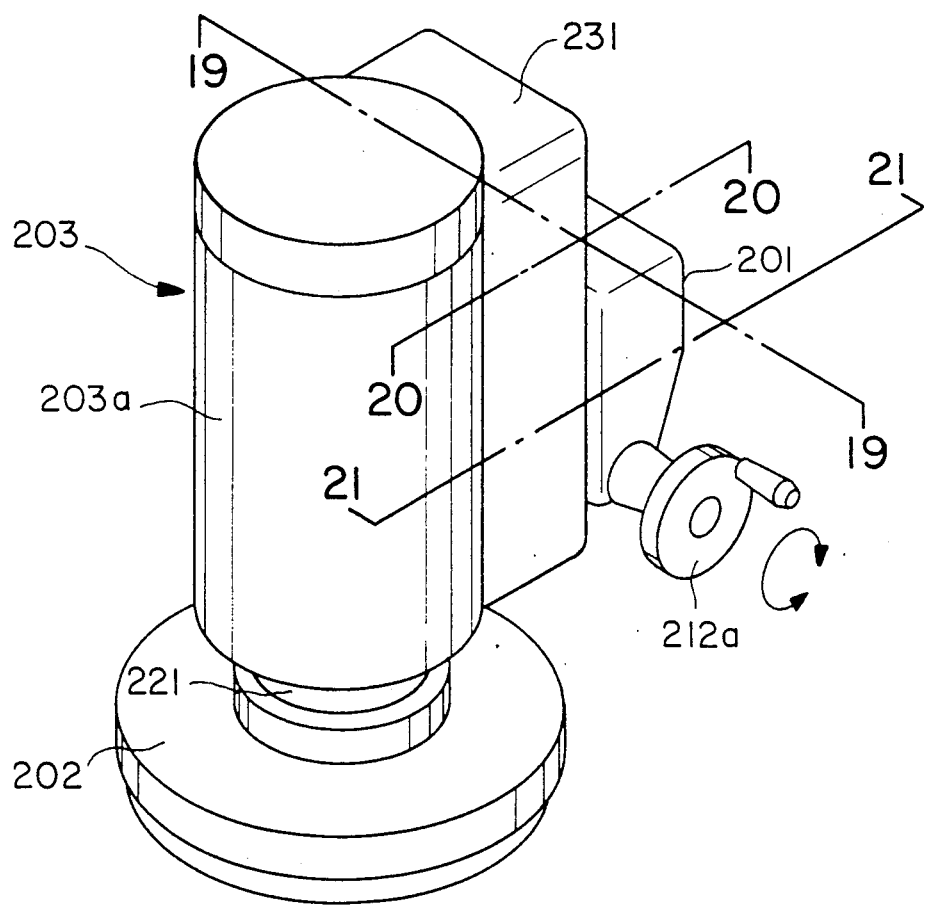
FIG. 18 is a perspective view of an alternate embodiment of the actuator for placing an applicator upon the patient.

Now the operation of the heat therapy system of the present embodiment is described in the following with reference to flow chart of FIG. 17.

First of all, the floppy disk of the patient who is going to be treated is inserted into the storage unit, and the data, such as the name, age and ID number of the patient and the name of his ailment, is read out from the floppy disk and displayed on the display unit 62 (Step 1 or ST1).

Then, the therapeutic data of the previous therapeutic sessions is read from the floppy disk (ST2) and displayed on the display unit for overview (ST3). The therapeutic data includes the points at which the thermo couple probes (not shown in the drawings) of the temperature measuring unit 70 are to be pierced, the temperature readings measured by the thermo couple probes at the parts of ailment or the like, the high frequency power output values, time periods of therapy, cooling water temperatures, cooling water flow rates, amounts of supplied cooling water, the positions and heights of the slide mats 12 and 13 of the bed parts 10 and 11, the rotary angle of the C-arm 23, and the data of the application of the applicators 10 and 11. The floppy disk may contain various comments as well as the general data on the patient and therapeutic data. The comments may include complaints made by the patient during the past therapeutic sessions.

After looking at the list of the therapeutic data displayed on the display unit 62, the operator enters from the input unit 61 that no change is to be made if the data is to be used as it is or otherwise enters whatever changes that are required. If no change is made, the determination result of ST4 is NO and the system flow branches off to ST5 where the next therapeutic data is selected from the past therapeutic data. If any changes are made, the system flow branches off to ST6, and the altered therapeutic data is inputted.

Figure 2:
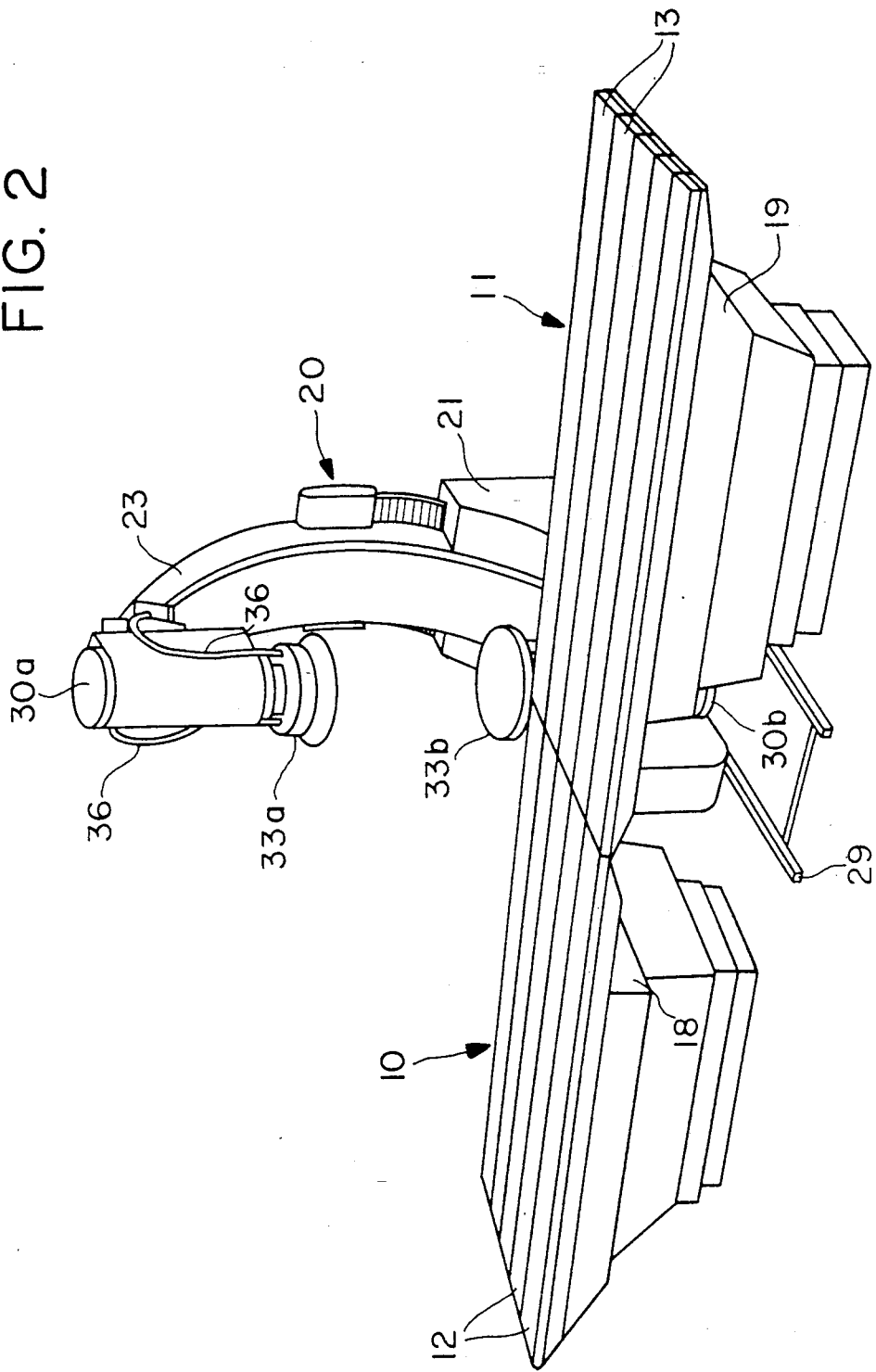
FIG. 2 is a perspective view of the state of the main part of the heat therapy system of FIG. 1 prior to the start of heat therapy.

When the step of data input in ST5 or ST6 is finished, a start message is displayed on the operation board display unit 42a (ST7). At this moment, the bed parts 10 and 11 and the applicator support unit 20 are in the condition illustrated in FIG. 2. In other words, the bed parts 10 and 11 are in their lower most positions (to facilitate placing the patient on the bed parts 10 and 11), and the slide mats 12 and 13 of the two bed parts 10 and 11 are abutting each other. Meanwhile, the applicator support unit 20 is in its retracted position, and the applicator mounts 30a and 30b are moved away in their releasing directions E.

Thereafter, the slide mats 12 are moved so as to define an opening between the two bed parts 10 and 11 (ST8). As mentioned earlier, the slide mats 12 and 13 are manually moved and, when they have reached the positions as dictated by the current therapeutic data selected at ST5 or modified at ST6, the slide mats 12 and 13 are stopped and fixed by the stop mechanism.

Then, the support bars 16 and 17 project from the bed parts 10 and 11 (ST9). At this moment, the patient is placed on the bed parts 10 and 11 by an assistant (ST10). Since the patient's body is supported by the support bars 16 and 17, the patient's body would not sag into the opening between the bed parts 10 and 11.

In ST11, both the bed parts 10 and 11 are lifted to a predetermined height. According to the present embodiment, the bed parts 10 and 11 continue to be lifted as long as the operator keeps pressing the operation button unit 42b, and the lifting motion of the bed parts 10 and 11 is automatically discontinued when the height of the bed parts 10 and 11 has reached the height which is specified in the current therapeutic data. If the operator releases his hand even before the bed parts 10 and 11 have reached the specified height, the lifting motion of the bed parts is discontinued but when the operation button unit 42b is operated again the lifting motion of the bed parts 10 and 11 is resumed.

This is to ensure safety, and may be called as semi-automatic. Alternatively, it is possible to display the target height and the current height on the display unit 42a so that the operation button unit 42b may be operated so as to equalize the target height and the current height or, in other words, strictly manually.

In ST12, the position of the applicator support unit 20 in the fore-and-aft direction is determined. In other words, when the operation button 42b is pressed, the applicator support unit 20 is moved forwardly, and then automatically stops as it reaches the prescribed position. In this case also, the system is semi-automatic in that the movement of the applicator support unit 20 is discontinued when the finger is released from the operation push button 42b from a safety point of view. Of course, it may also be performed strictly manually.

In ST13, the rotational angle of the C-arm 23 is determined by pressing the operation button 42b also in a semi-automatic fashion. In ST14, the applicator mount 30b is drivingly moved in the direction of the applicator application D. In ST15, it is determined whether the applicator 33b has reached the support bars 16 and 17 or not, and if not the movement of the applicator 33b is continued. When the applicator 33b has reached the support bars 16 and 17, the system flow branches off to ST16 and the applicator mount 33b is temporarily kept stationary. Thereafter, the support bars 16 and 17 and withdrawn (ST17), and the applicator mount 30b is again moved in the direction of applicator application until it is automatically stopped at a prescribed position at which the applicator 33b is pressed upon the patient P (ST18). The application of the applicator 33b is also performed semi-automatically (or manually).

In ST19, the application of the applicator 33a is semi-automatically (or manually) performed. In other words, while the operation button 42b is pressed, the applicator mount 30a is driven in the application direction D until it is automatically stopped at the prescribed position where the applicator 33a is pressed upon the patient P (refer to FIG. 15).

In ST20, high frequency electric current of a prescribed power output is applied to the applicators 33a and 33b for a prescribed period of time for heating purpose. Meanwhile, cooling water is circulated in the applicators 33a and 33b by the cooling system 50 for cooling the electrodes 34 and the skin of the patient. The temperature and flow rate of the cooling water and the amount of cooling water supplied to the applicators 33a and 33b are controlled to the values prescribed in the aforementioned therapeutic data.

When the heating process is finished, the current therapeutic data and other data is stored in the floppy disk (ST21) and the applicators 33a and 33b are removed in the reverse order to the steps of ST8 through ST19 (ST22).

In the above described embodiment, a floppy disk drive was used as a storage unit, but other units such as hard disk drives, optical disk drives and so on can also be used among other possible design modifications.

Figure 19:
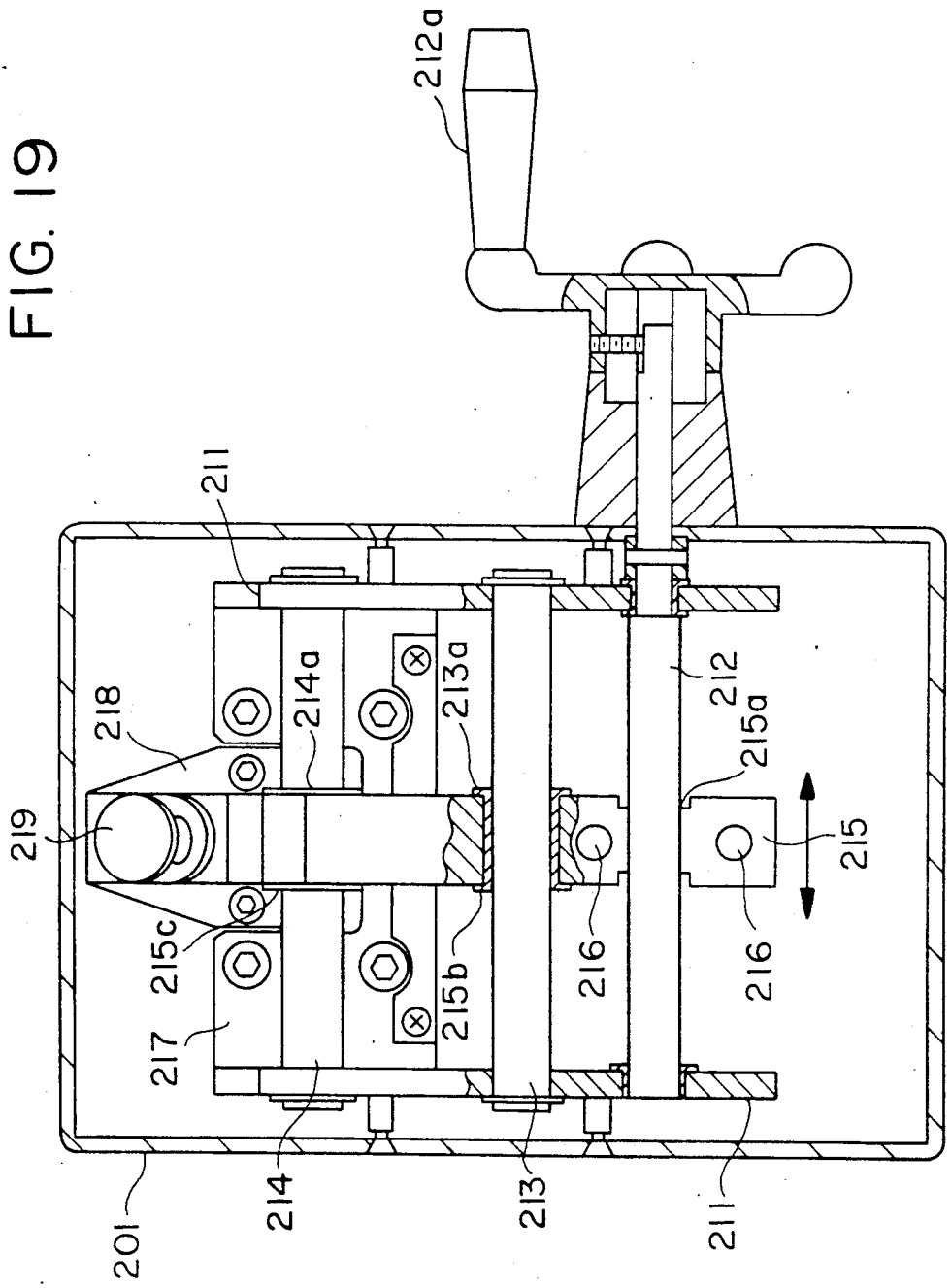
FIG. 19 is a sectional view taken along line 19—19 of FIG. 18.
Figure 20:
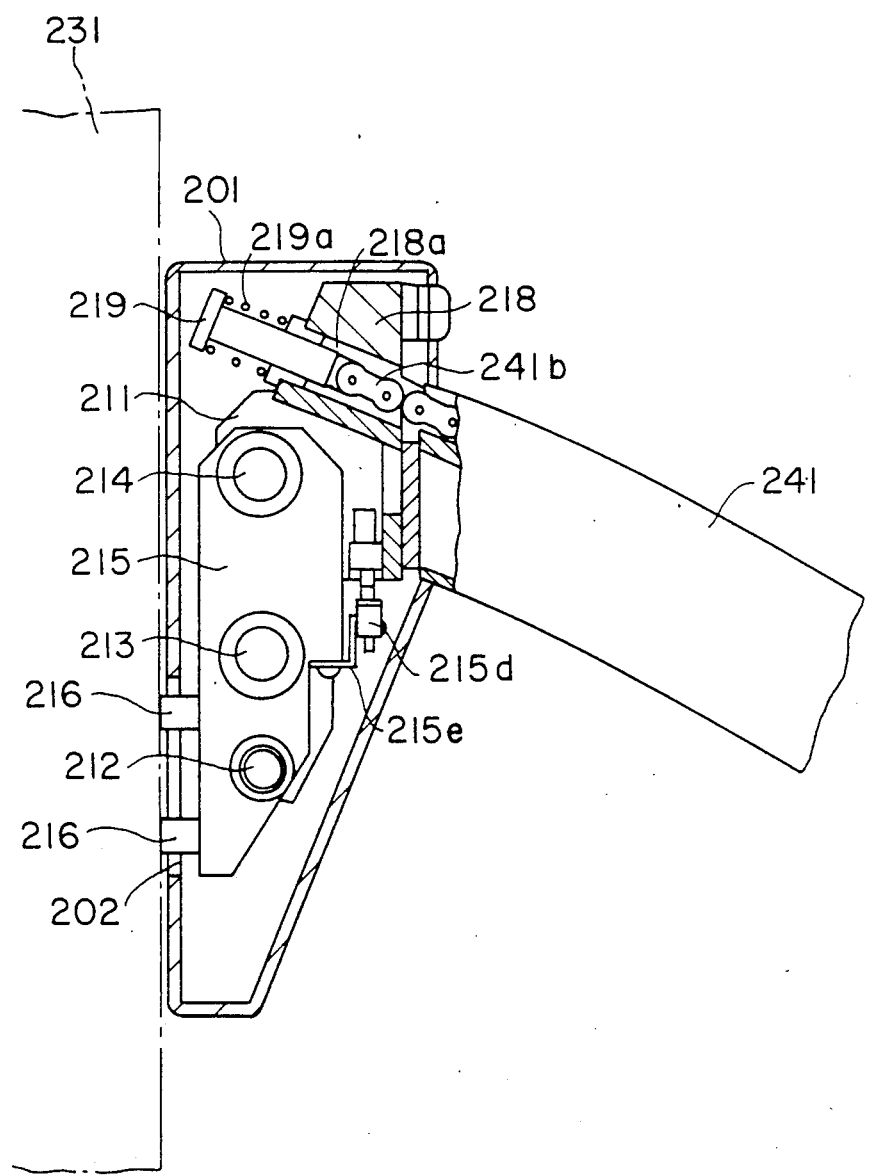
FIG. 20 is a sectional view taken along line 20—20 of FIG. 18.

FIGS. 18 through 21 show an alternate embodiment of the applicator mount assembly. This electrode mount assembly comprises an electrode 202, an electrode mount 203 and a slide unit 201, and is mounted on a free end of a curved arm 241. As shown in FIG. 20, an end 219 of a chain 241b for moving the arm 241 is engaged within the slide unit 201 by way of a compression coil spring 219a which serves as a buffer member at the terminal ends of the movement of the arm 241. This chain 241 is driven by a sprocket not shown in the drawings in the same manner as the chain 25 along with the arm 23 is driven by the sprocket 24c in the embodiment illustrated in FIG. 3.

Now, the electrode mount 203 is received in a cylindrical casing 103a, and is provided with a mounting bore for receiving the mounting rod 221 of the electrode 202. The electrode mount 203 is provided with a linear drive unit for moving the electrode mount 203 into and out of the cylindrical casing 203a, a angular adjustment unit for angularly displacing the electrode mount, and a high frequency power supply unit for applying high frequency electric current to the electrode 202 which are not shown in the drawings.

The slide unit 201 is disposed between the arm 241 and the electrode mount 203 or the casing 203a thereof. The slide unit 201 is received its own casing 201a, and an end of this casing is attached to the electrode mount 203 or its casing 203a while its other end is attached to the arm 241.

As shown in FIG. 19, a pair of wall members 211 are arranged so as to oppose each other in the casing 201a. A threaded rod 212 and a pair of smooth rods 213 and 214 extend between the two wall members 211. A slider member 215 is disposed between the two wall members 211 in parallel relationship, and is provided with a threaded hole 215a receiving the threaded rod 212 and a pair of smooth holes 215 and 215c receiving the smooth rods 213 and 214 via bushes 213a and 214a, respectively. An end of the threaded rod 212 extends laterally out of the casing 201a and is provided with a crank handle 212a for rotating the threaded rod 212.

Therefore, as the handle 212a is turned manually, the slider member 215 can move linearly between the two opposing wall members 211 according to the direction of the rotation of the theaded rod 212.

Figure 21:
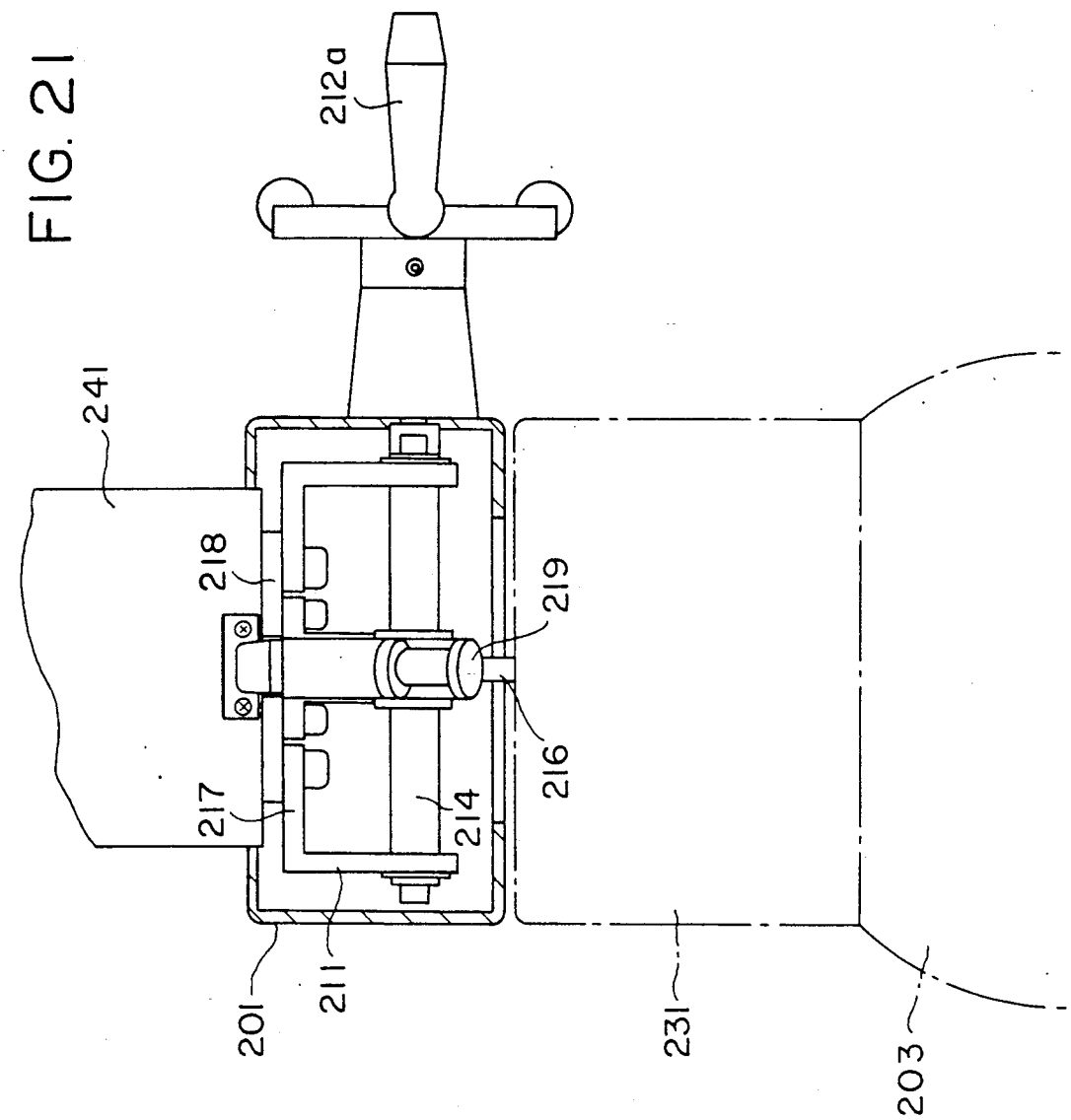
FIG. 21 is a sectional view taken along line 21—21 of FIG. 18.

As shown in FIGS. 19 through 21, the wall members 212 are securely attached to a backet 217 which is in turn securely attached to the arm 214 by way of a mounting member 218. As shown in FIG. 20, this mounting member 218 is provided with an opening 218a for passing an end of the chain 241b therethrough. The outermost end of the chain 241b is connected to a rod member 219 which is urged by the compression coil spring 219a for accommodating abrupt tensioning of the chain 218a. Referring to FIG. 20, a center detection micro switch 215d is mounted on the arm mounting member 218, and the slider member 215 is provided with a contact piece 215e which contacts the micro switch 215d when the slider member 215 is at the middle point of the threaded rod 212.

Figure 22:
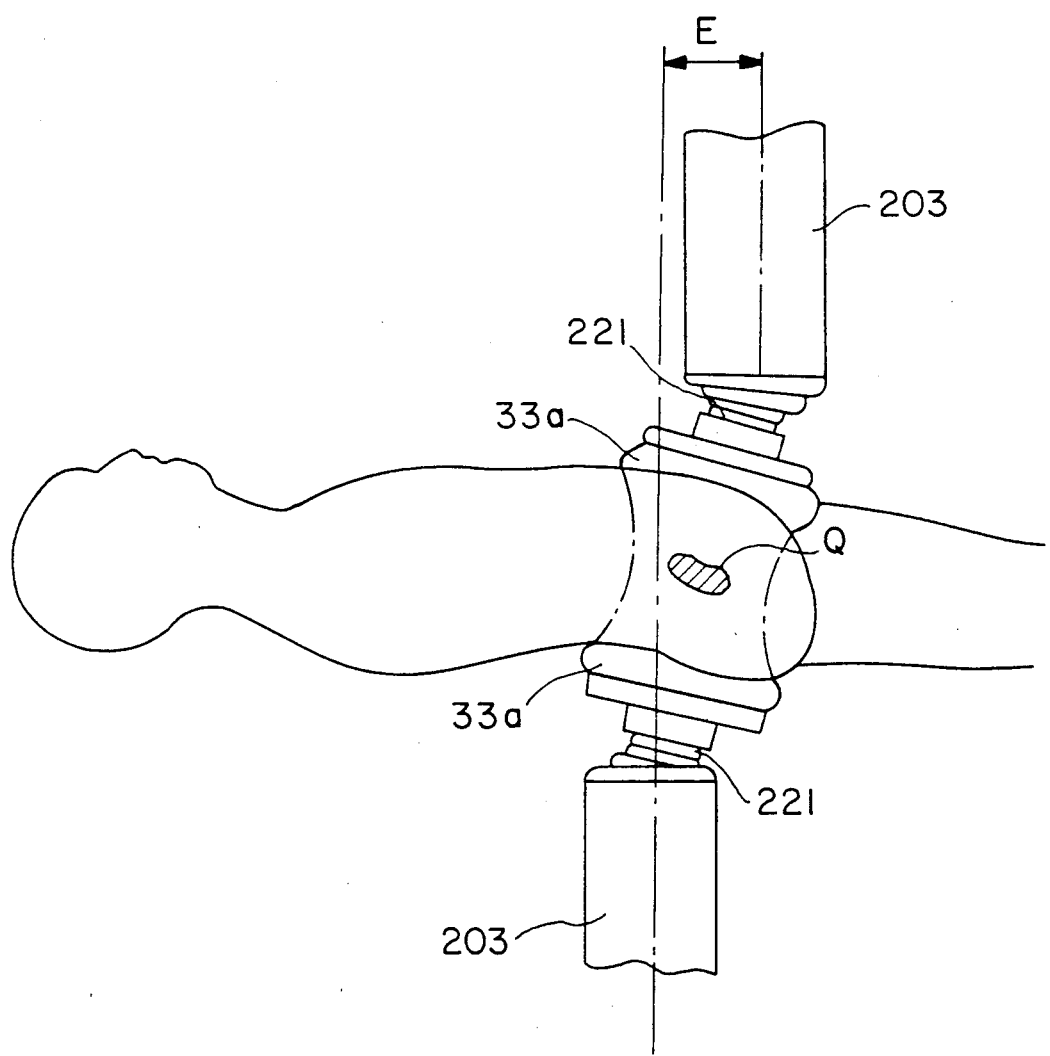
FIG. 22 is a schematic side showing how the applicators may be placed upon the patient by using the actuators illustrated in FIGS. 18 through 21.

According to this applicator mount structure which can offset the center line of the applicator or the electrode thereof, it is assumed that the center lines of the pair of electrodes 202 mounted on either end of the arm 241 are in alignment on a common line. If the ailing part Q is out of alignment with the applicators 33a and 33b as shown in FIG. 22 for instance due to the non-horizontal contour of the patient's body, the upper applicator 33a may be laterally displaced by distance E by turning the handle 212a. The rotation of the handle 212a is transmitted to the screw rod 212 which in turns moves the slider member 215 laterally with respect to the arm 241. This movement of the slider member 215 is transmitted to the mounting plate 231, and the electrode mount 203 along with the applicator 33a is moved laterally with respect to the original axial line of the applicator 33a. At the same time, the applicators 33a and 33b are pivoted so that they may oppose each other along a common line, and a desired application of the high frequency electric current may be performed.

Thus, according to the present embodiment, the applicators may be directed in any direction so that ailing parts of any location may be properly aimed with the applicators at a close range or, in other words, with a minimum distance between the two applicators.

Figure 24:
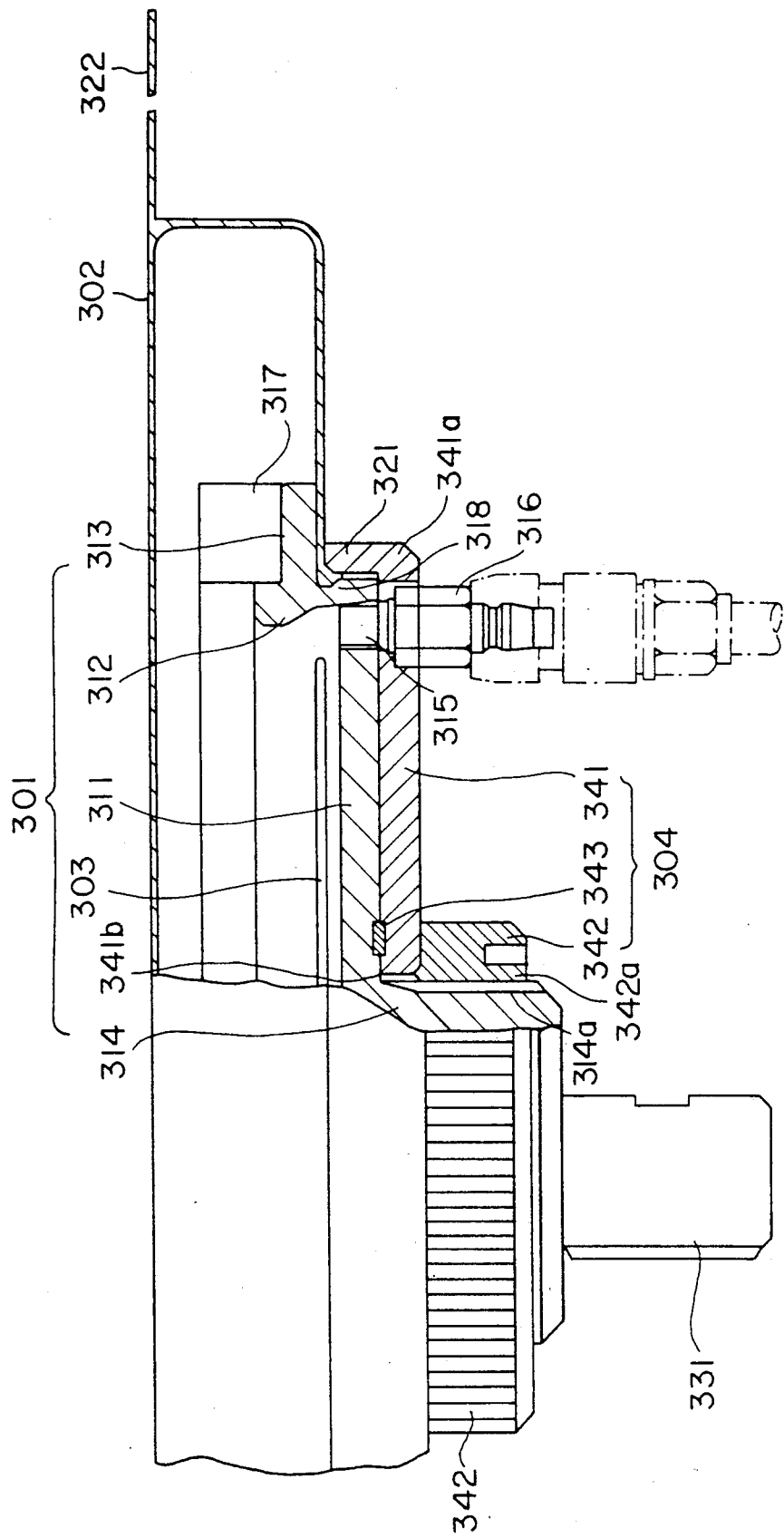
FIG. 24 is a partly broken away, fragmentary side view of the bolus bag assembly shown in FIG. 23.
Figure 23:
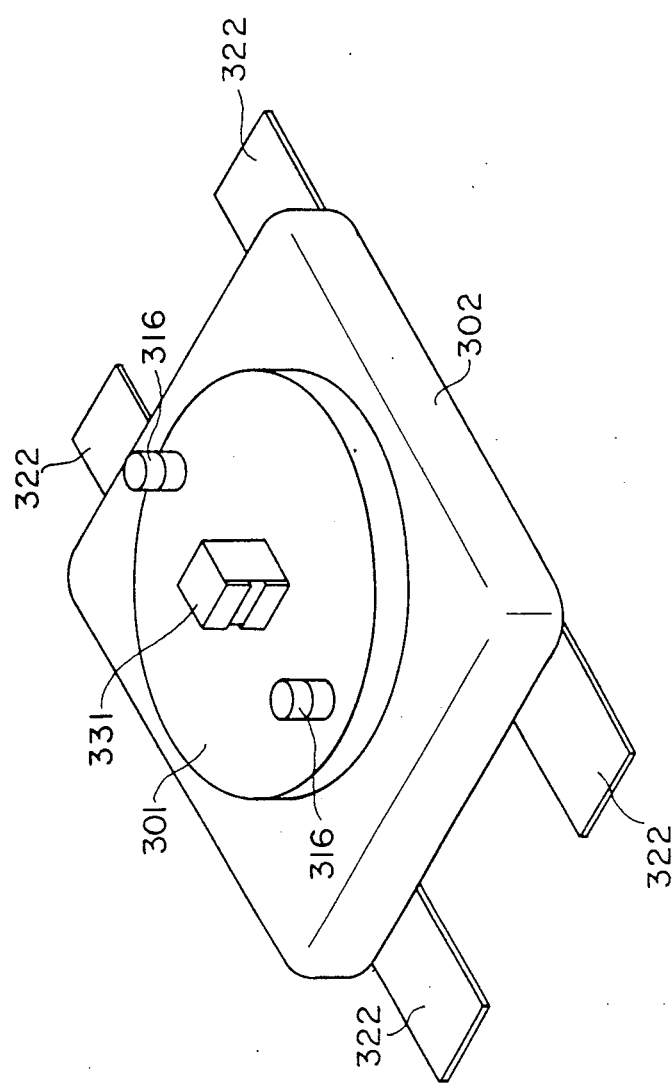
FIG. 23 is an alternate embodiment of the bolus bag assembly according to the present invention.

The embodiment of the applicator according to the present invention illustrated in FIGS. 23 and 24 is provided with a circular electrode mount 301, a bolus bag 302 detachably attached to the electrode mount 301, and securing means 304 for achieving the detachable attachment of the bolus bag 302 to the electrode mount 301.

As shown in the sectional view of FIG. 24, the electrode mount comprises a disk portion 311 and a short axial flange 312 extending form its periphery. Further, a radial flange 313 extends from the outer circumferential surface of the axial flange 312. The central part of the disk portion 311 is provided with a cylindrical part 314 for passing an electrode mounting rod 331, and an outer circumferential part of the disk portion 311 provided with an opening 315 into which is threaded a fluid conduit coupler 316 for supplying cooling fluid into the bolus bag 302. An annular pad ring 317 is fitted onto the axial flange 312 and abuts the radial flange 317 at its end surface. Further, the outer circumferential surface of the axial flange 312 adjoining the rear surface of the radial flange 313 is provided with an annular groove 318 for fitting an open end of the bolus bag 302.

The electrode 303 consists of a disk which is slightly smaller than the axial flange 312, and is additionally provided with the electrode mounting rod 331 projecting from a central part of the electrode 303 which is passed out of the cylindrical portion 312. This projecting mounting rod 331 is to be mechanically mounted on the electrode mount of the arm or the gantry of the high frequency heat therapy system to which this bolus bag is applied, and is electrically connected to the high frequency electric power supply unit provided in the electrode mount.

The bolus bag 302 may consist of a highly elastic and flexible bag made of silicone rubber, latex rubber or other similar materail, and its opening end is provided with a bead 321. Thus, by stretching this bead 321, the open end of the bolus bag 302 may be fitted onto the annular groove 318 of the axial flange 312. Cooling water which may consist of salt water, pure water or the like is introduced from the fluid coupling 316 into the bolus bag 302 and is circulated therein.

The securing means 304 comprises a pressure plate 341, a pressure ring 342 and a highly elastic annular pusher pad 343. The pressure plate 341 is provided with an axial flange 341a defining an opening 341b which is to be fitted onto the rear end of the axial flange 312 interposing the bead 321 therebetween. The pressure ring 342 is provided with a threaded inner circumferential surface 342a which is threaded with the corresponding threaded portion 314a provided in the outer circumferential surface of the cylindrical portion 314. The annular pusher pad 343 is interposed between the rear surface of the disk portion 311 and the front surface of the pressure plate 341.

One of the primary features of this applicator is found in the fact that the bolus bag 302 is substantially greater than the electrode mount 301 and is therefore provided with a significantly larger area of contact as compared with conventional bolus bags.

FIGS. 23 and 23 illustrate an applicator according to a preferred embodiment of the present invention. This applicator comprises a relatively flat bolus bag 302 to accommodate liquid therein having a rectangular shape as seen in plan view. It has a relatively large area as compared with a circular and central electrode mount 301 so that the bolus bag 302 may significantly protrude laterally from the electrode mount 301. Therefore, this bolus bag has a substantially same thickness as those of conventional bolus bags but has a considerably larger capacity due to the added volume of the part protruding laterally from the electrode mount 301.

Figure 25:
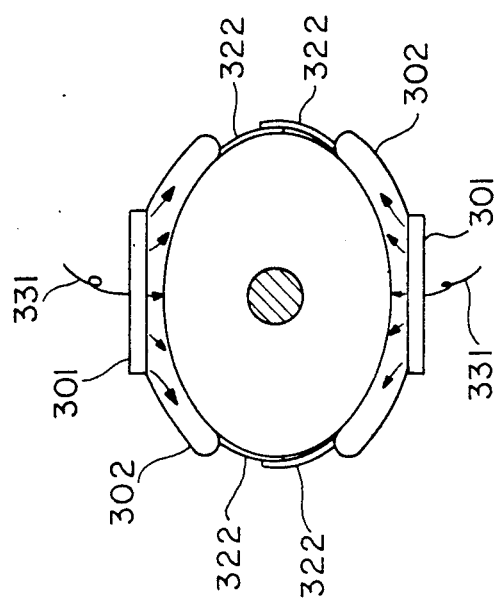
FIG. 25 is a schematic side showing how the bolus bag assemblies may be placed upon the patient according to the embodiment illustrated in FIGS. 23 and 24.

Further, according to this embodiment, two pairs of attaching bands 322 extend laterally from either side of the lower surface of the bolus bag 302. The attaching bands 322 as well as the bolus bag 302 itself are made of silicone rubber, and the attaching bands 322 may be integrally formed with the bolus bag 302. The attaching bands 322 may be provided with attaching means such as Velcro (trademark) tapes, buckles and so on for connecting the attaching bands 322 with the corresponding attaching bands of the other bolus bag which is not shown in the drawings to the end of achieving a favorable state of contact between the applicators and the human body as shown in FIG. 25.

Figure 26:
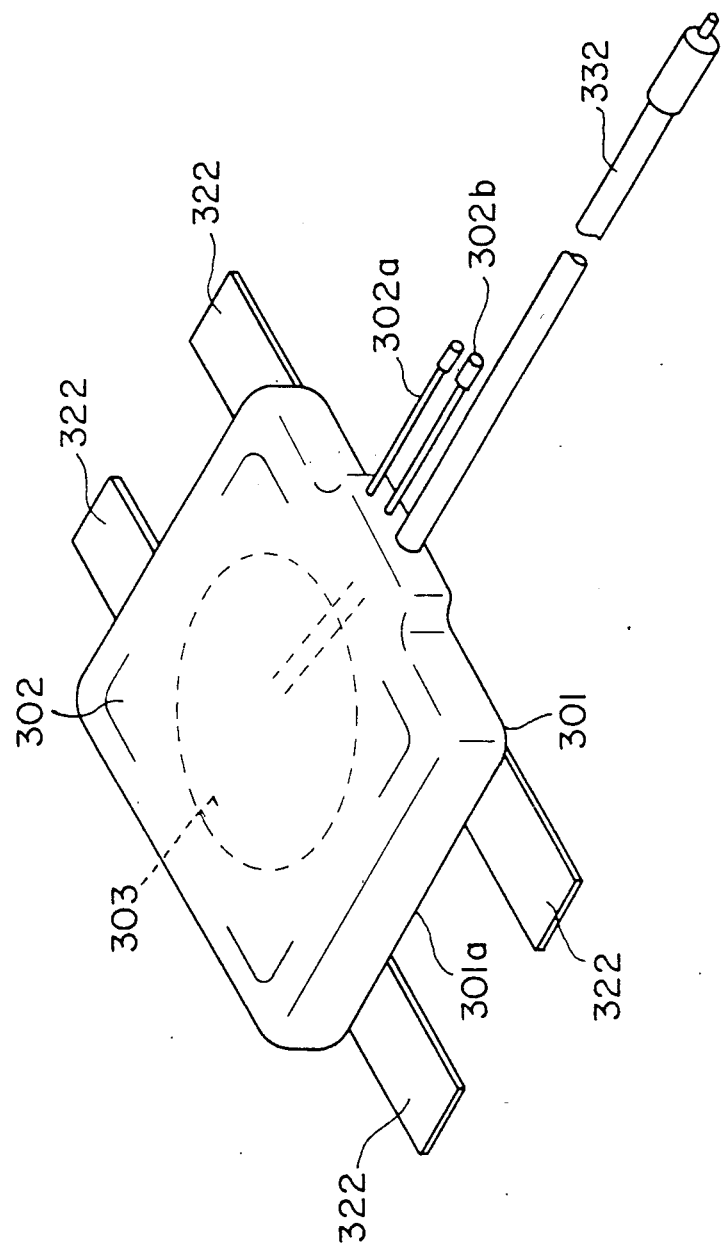
FIG. 26 is yet another embodiment of the bolus bag assembly according to the present invention.

FIG. 26 shows an alternate embodiment of the applicator which is adapted as a compact portable applicator. This applicator comprises a disk shaped electrode 303, and each surface of the electrode 303 is covered by insulation sheets of the same size as the electrode 303. These insulation sheets serves as the electrode mount 301. The lower insulation sheet 301a is provided with a rectangular extension having a relatively large area. The bolus bag 302 is provided with a rectangular lower opening which is larger than the insulation sheet 301a. In other words, the bolus bag 302 has a substantially same planar area as the extension of the lower insulation sheet, and the periphery of the lower opening of the bolus bag 302 is attached to the extension of the lower insulation sheet 301a, thereby enclosing the electrode 303 in the bolus bag 302. Thus, as seen in plan view, the bolus bag 302 extends outwardly from the insulation sheet (electrode mount) 301 having the substantially the same area as the electrode 303.

A lead wire 332 and 302b for the electrode 303 extends outwardly from a side portion of the bolus bag 302. Also, a cooling water inlet tube 302a and a cooling outlet tube 302b extend from the bolus bag 302 and are connected to a cooling water supply unit not shown in the drawing.

According to this applicator for high frequency heat therapy, the bolus bag 302 is larger than the electrode mount (the insulation sheet 301a in the case of the portable applicator or the electrode mount in the case of the gantry or arm type applicator shown in FIGS. 23 and 24. In other words, the bolus bag 2 is selected to be comparable to conventional water boluses which are separately provided so as to be interposed between an applicator and the body part. Therefore, the area of contact is significantly increased, and even when the surface of the bodily part of interest is provided with a projection such as a tumor, the bolus bag 302 may be applied to this part achieving a favorable state of contact therebetween. Therefore, the edge effect can be avoided. Further, since the thickness of the bolus bag 302 is no more than those of conventional bolus bags and, therefore, the distance between the applicators is not increased, a high power efficiency can be achieved without incurring any significant power loss.

In particular, by providing attachment bands 322 on either side of the applicator and connecting the attachment bands 322 of the mutually opposing applicators, the bolus bags 302 can extends outwardly and closely follow the contour of the body part, and a favorable state of contact can be achieved.

Further, since the size of the bolus bag is increased as compared with the electrode mount 301 and the area of contact is increased, when the applicators are applied to a patient from above and below as shown FIG. 25, air bubbles which may be present in the lower bolus bag migrates to the outer periphery of the bolus bag and therefore does not reduce the power efficiency of the the supply of high frequency electric current to the ailing part. In the case of the upper applicator also, air bubbles tend to migrate into the electrode mount 301 and again would not reduce the power efficiency of the applicator.

As described above, according to the heat therapy unit of the present invention, variations in the height of the therapeutic table and the state of applicator application can be minimized with the result that a high level of reproducibility can be attained and, therefore, contributions of various therapeutic data to the effectiveness of heat therapy can be easily analyzed.

Further, since the operation is simplified, the operator can pay more attention to the state and well being of the patient than was possible heretofore, and the safety level may be improved.

Additionally, the therapeutic data when using therapeutic systems of the same make can be unified, and rational construction of a line of therapeutic systems is made possible. For instance, when two therapeutic systems of the same make are installed in two different sections of a same hospital, the storage media used in one of the systems can be used in the other system installed in the different section, and a therapy based on the same therapeutic data can be performed.

Further, by permitting the overview of the therapeutic data, selection of most effective therapeutic data is made possible substantially without any difficulty.

What we claim is:

1. A high frequency heat therapy system, comprising: an applicator equipped with an electrode and a bolus bag;

high frequency generator means for generating high frequency electric current that is to be applied to said electrode;

cooling fluid circulating means for circulating cooling fluid through said bolus bag;

a therapeutic table for adjustably supporting a patient;

applicator support means for adjustably applying said applicator to said patient;

temperature measuring means for measuring a temnperature of a bodily part of said patient that is to be treated;

temperature control means for processing a temperature signal from said temperature measuring means and controlling said high frequency generator means and said cooling fluid circulating means;

therapeutic data input means for specifying therapeutic data including data related to positioning of said therapeutic table and said applicator support means;

therapeutic data storage means for storing therapeutic data including said data related to positioning of said therapeutic table and said applicator support means;

drive control means for drivingly controlling said therapeutic table and said applicator support means according to said data related to positioning of said therapeutic table and said applicator support means stored in said storage means; and central control means for transmitting data stored in said therapeutic data storage means and, if any, said therapeutic data specified by said therapeutic data input mean to said drive control means.

2. A high frequency heat therapy system according to claim 1, wherein said therapeutic data includes a value of high frequency power output.

3. A high frequency heat therapy system according to claim 1, wherin said central control means include a display unit for displaying various data on each particular patient who is going to be treated.

4. A high frequency heat therapy system according to claim 1, wherein said therapeutic table comprises a pair of mutually opposed bed parts which are separated by a therapeutic region wherein a bodily part to be treated is placed and retractable support bars extending from mutually opposed parts of said bed parts.

5. A high frequency heat therapy system according to claim 4, wherein each of said support bars comprises a bar member which can move into and away from said therapeutic region, and a belt extending over an upper surface of said bar member and having one end attached to a part of said bed part adjacent to a base end portion of said bar member and another end adapted to be wound upon a winding pulley.

6. A high frequency heat therapy system according to claim 4, wherein said support bars comprise a plurality elongated bar members arranged in mutually parallel relationship, and each of said bar members is provided with a rack which meshes with a pinion which is common to at least two of said bar members.

7. A high frequency heat therapy system according to claim 1, wherein said applicator support means comprises an arcuate arm extending around the patient to be treated, and is guided for angular movement along its curved axial line.

8. A high frequency heat therapy system according to claim 1, wherein said applicator support means comprises angular displacement means for permitting angular displacement of said applicator about a pivot point at a base end portion of said applicator, and a linear displacement means for moving said applicator toward and away from the patient to be treated.

9. A high frequency heat therapy system according to claim 1, wherein said applicator support means further comprises an elastic buffer means for accommodating movement of the patient when said applicator is applied to said patient.

10. A high frequency heat therapy system according to claim 9, wherein said applicator support means further comprises drive stop means for stopping movement of said applicator toward the patient to be treated when deformation of said buffer means has exceeded a certain limit.

11. A high frequency heat therapy system according to claim 1, wherein said applicator support means comprises lateral displacement means for displacing said applicator laterally from an axial center line running through said electrode and said applicator.

12. A high frequency heat therapy system according to claim 1, wherein said bolus bag is substantially larger than said electrode as seen in plan view.

13. A high frequency heat therapy system according to claim 1, wherein said bolus bag is provided with attaching bands extending laterally therefrom.

* * * * *

UNITED STATES PATENT AND TRADEMARK OFFICE
CERTIFICATE OF CORRECTION

PATENT NO. : 5,046,495                              Page 1 of 2

DATED : September 10, 1991

INVENTOR(S) : Takahashi et al

It is certified that error appears in the above-identified patent and that said Letters Patent is hereby corrected as shown below:

Column 13, line 9, change "slide mat" to --support bar--.
Column 13, line 10, change "support bar" to --slide mat--.
In the drawings, Sheet 13, Fig. 16, the blocks corresponding to numerals 46a and 46b, which read "support bar control unit", should read --slide mat control unit--, each occurrence, and appear as follows:

UNITED STATES PATENT AND TRADEMARK OFFICE
CERTIFICATE OF CORRECTION

PATENT NO. : 5,046,495

DATED : September 10, 1991

INVENTOR(S) : Takahashi et al.

It is certified that error appears in the above-identified patent and that said Letters Patent is hereby corrected as shown below:

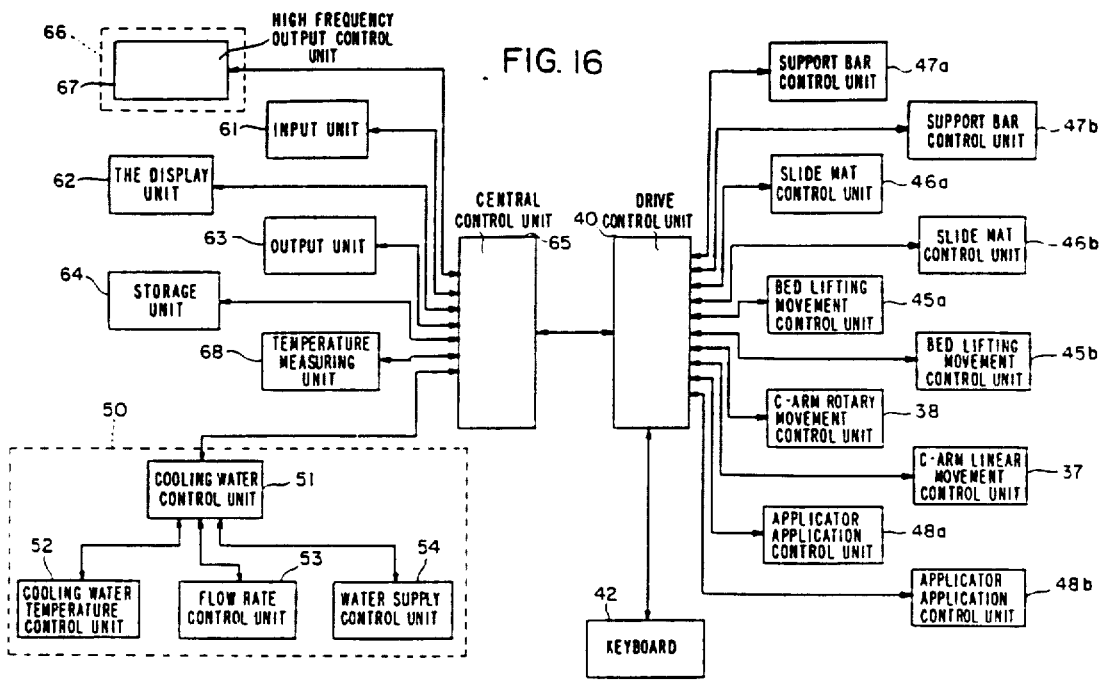

Signed and Sealed this

Twentieth Day of April, 1993

Attest:

MICHAEL K. KIRK

Attesting Officer

Acting Commissioner of Patents and Trademarks